United States Patent
Nie et al.

(10) Patent No.: US 11,285,539 B2
(45) Date of Patent: Mar. 29, 2022

(54) SYNTHESIS AND FUNCTIONALIZATION OF HIGHLY MONODISPERSED IRON AND CORE/IRON OXIDE SHELL MAGNETIC PARTICLES WITH BROADLY TUNABLE DIAMETER

(71) Applicants: University of Maryland, College Park, College Park, MD (US); University of Maryland, Baltimore, Baltimore, MD (US)

(72) Inventors: Zhihong Nie, Greenbelt, MD (US); Radi Masri, Ellicott City, MD (US)

(73) Assignees: University of Maryland, College Park, College Park, MD (US); University of Maryland, Baltimore, Baltimore, MD (US)

( * ) Notice: Subject to any disclaimer, the term of this patent is extended or adjusted under 35 U.S.C. 154(b) by 313 days.

(21) Appl. No.: 16/300,299

(22) PCT Filed: May 12, 2017

(86) PCT No.: PCT/US2017/032485
§ 371 (c)(1),
(2) Date: Nov. 9, 2018

(87) PCT Pub. No.: WO2017/197310
PCT Pub. Date: Nov. 16, 2017

(65) Prior Publication Data
US 2019/0118265 A1    Apr. 25, 2019

Related U.S. Application Data

(60) Provisional application No. 62/336,131, filed on May 13, 2016.

(51) Int. Cl.
  *B22F 9/24*    (2006.01)
  *B22F 1/02*    (2006.01)
  (Continued)

(52) U.S. Cl.
  CPC .................. *B22F 9/24* (2013.01); *A61C 8/00* (2013.01); *A61K 41/0052* (2013.01);
  (Continued)

(58) Field of Classification Search
  None
  See application file for complete search history.

(56) References Cited

U.S. PATENT DOCUMENTS 6,676,963 B1   1/2004  Lanza et al.
6,685,730 B2   2/2004  West et al.
(Continued)

FOREIGN PATENT DOCUMENTS

WO   WO 2014174328 A1   10/2014

OTHER PUBLICATIONS

International Search Report and Written Opinion for International Application No. PCT/US2017/032485, Korean Intellectual Property Office, Republic of Korea, dated Jul. 11, 2017, 14 pages.
(Continued)

*Primary Examiner* — George Wyszomierski
(74) *Attorney, Agent, or Firm* — Sterne, Kessler, Goldstein & Fox P.L.L.C.

(57) ABSTRACT

Provided are methods for preparing iron nanoparticles and to iron nanoparticles produced by those methods. The invention also provides methods for coating the iron nanoparticles with oxides and functionalizing the iron nanoparticles with organic and polymeric ligands. Additionally, the invention provides methods of using such iron nanoparticles.

8 Claims, 24 Drawing Sheets

(51) Int. Cl.

| | |
|---|---|
| *A61K 41/00* | (2020.01) |
| *B22F 1/00* | (2022.01) |
| *A61K 47/69* | (2017.01) |
| *A61C 8/00* | (2006.01) |
| *A61C 13/083* | (2006.01) |

(52) U.S. Cl.
CPC ...... *A61K 47/6923* (2017.08); *A61K 47/6929* (2017.08); *B22F 1/0018* (2013.01); *B22F 1/02* (2013.01); *A61C 13/083* (2013.01)

(56) References Cited

U.S. PATENT DOCUMENTS

| | | | |
|---|---|---|---|
| 7,459,145 B2 | 12/2008 | Bao et al. | |
| 8,343,627 B2 | 1/2013 | Zhong et al. | |
| 9,390,845 B2 | 7/2016 | Rowe et al. | |
| 2006/0237029 A1* | 10/2006 | Yang | B09C 1/08 134/1 |
| 2007/0290175 A1* | 12/2007 | Kim | B22F 1/025 252/500 |
| 2008/0087137 A1 | 4/2008 | Shim et al. | |
| 2008/0091054 A1 | 4/2008 | Choi et al. | |
| 2010/0025874 A1 | 2/2010 | Apel et al. | |
| 2011/0104073 A1 | 5/2011 | Zeng et al. | |
| 2011/0313059 A1* | 12/2011 | Blosi | B01J 13/0043 516/97 |
| 2012/0012778 A1 | 1/2012 | Tilley et al. | |
| 2013/0071558 A1 | 3/2013 | Zhong et al. | |

OTHER PUBLICATIONS

Aoshima, H., et al., "Fabrication of Fe nanoparticles with sizes ranging from 30 to 170 nm by gas flow sputtering," *J. Appl. Physics* 105.07B519 (3 pages), American Institute of Physics, United States (2009).

Fu, L.-S., et al., "Synthesis of hexagonal Fe microflakes with excellent microwave absorption performance," *CrystEngComm* 14:6827-6832, The Royal Society of Chemistry, United Kingdom (2012).

D. L. Huber, "Synthesis, Properties, and Applications of Iron Nanoparticles," *Small* 1(5):482-501, Wiley-VCH Verlag GmbH & Co., Germany (2005).

Peng, S., et al., "Synthesis and Stabilization of Monodisperse Fe Nanoparticles," *J. Am. Chem. Soc.* 128:10676-10677, American Chemical Society, United States (2006).

Sun, G., et al., "Hierarchical Dendrite-Like Magnetic Materials of $Fe_3O_4$, $\gamma$-$Fe_2O_3$, and Fe with High Performance of Microwave Absorption," *Chemistry of Materials* 23:1587-1593, American Chemical Society, United States (2011).

Wang, L., et al., "Electrospun hollow cage-like $\alpha$-$Fe_2O_3$ microspheres: synthesis, formation mechanism, and morphology-preserved conversion to Fe nanostructures," *CrystEngComm* 16:10618-10623, The Royal Society of Chemistry, United Kingdom (2014).

Wang, L., et al., "Facile synthesis of Fe@$Fe_2O_3$ nanochains exhibiting high heating efficiency in magnetic hyperthermia," *Journal of Alloys and Compounds* 681:50-56, Elsevier B.V., Netherlands (2016).

Zhan, X., et al., "Facile preparation of Fe nanochains and their electromagnetic properties," *RSC Advances* 3:15966-15970, The Royal Society of Chemistry, United Kingdom (2013).

\* cited by examiner

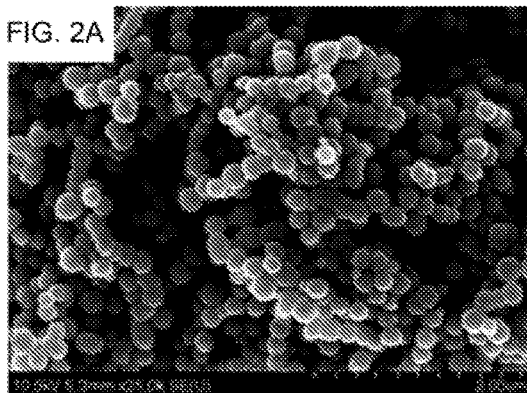
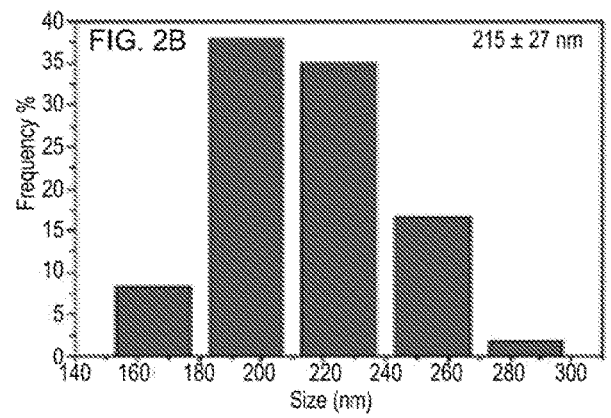
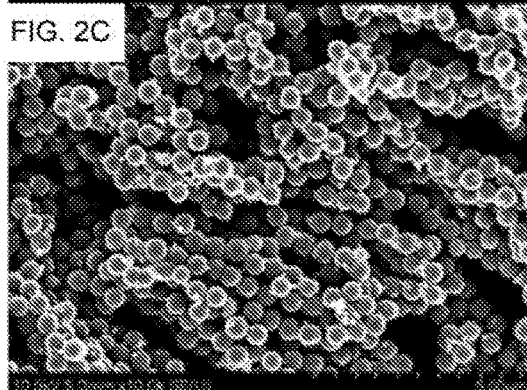
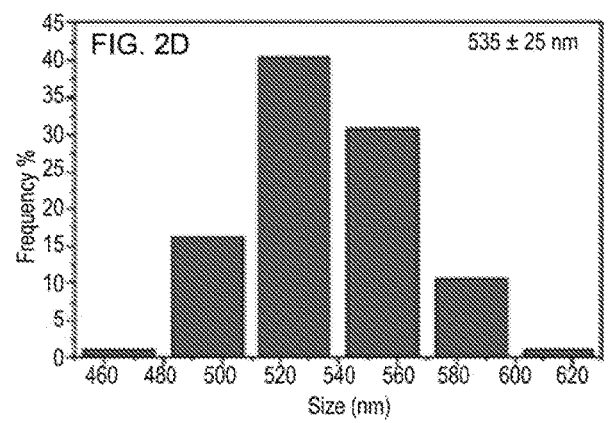
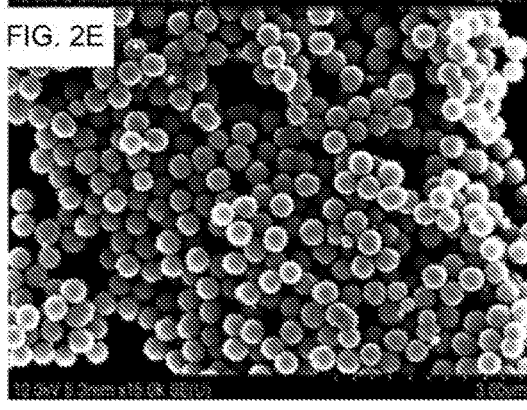
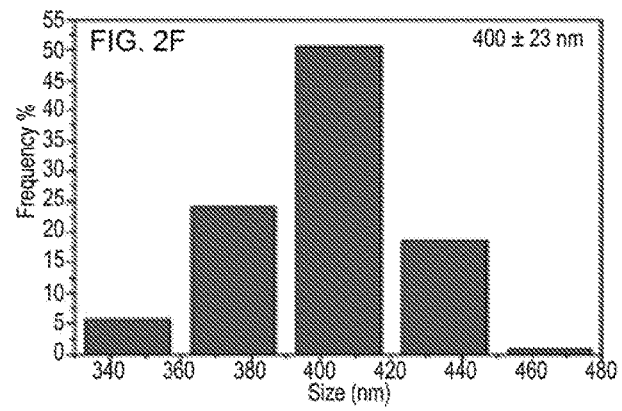

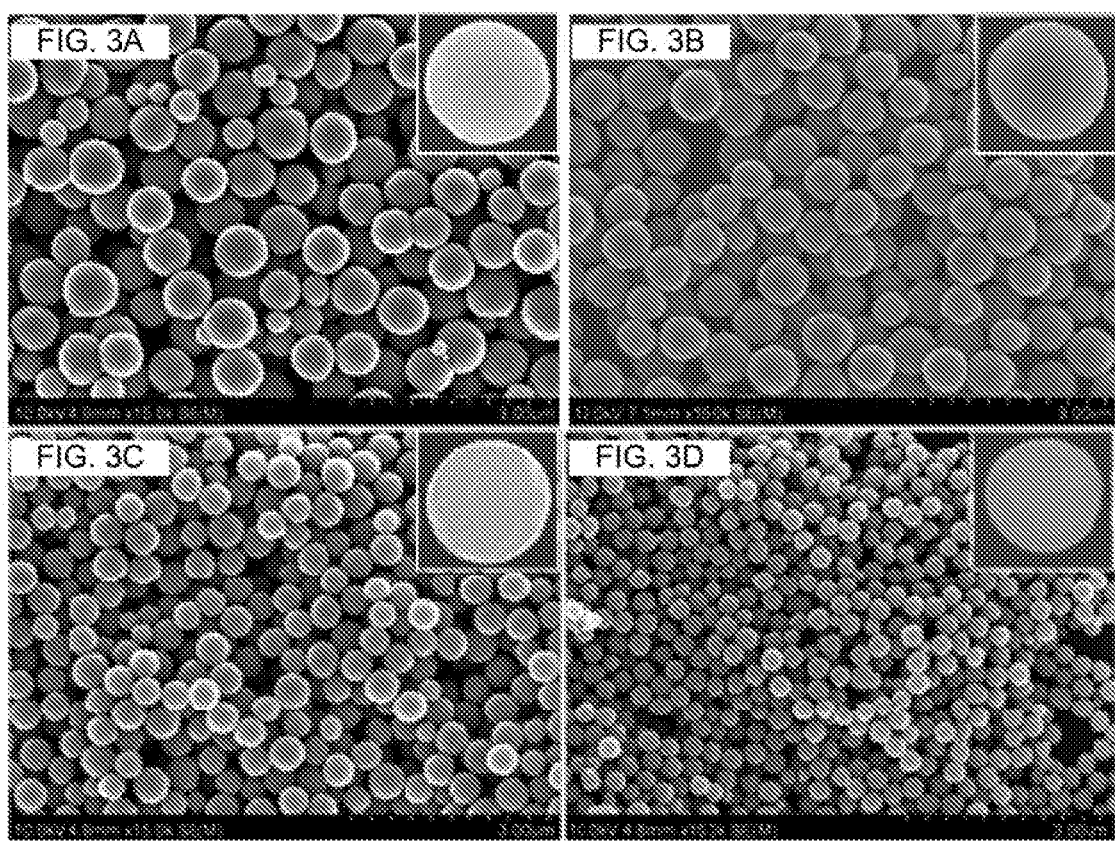

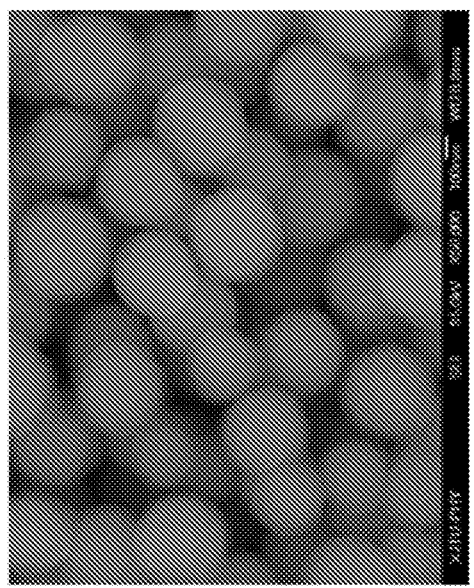
FIG. 11C
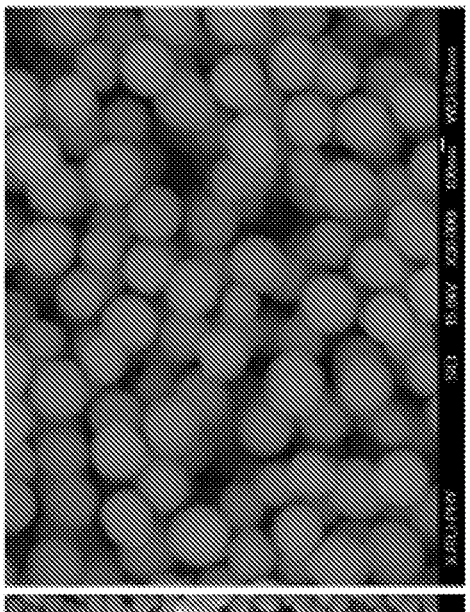
FIG. 11B
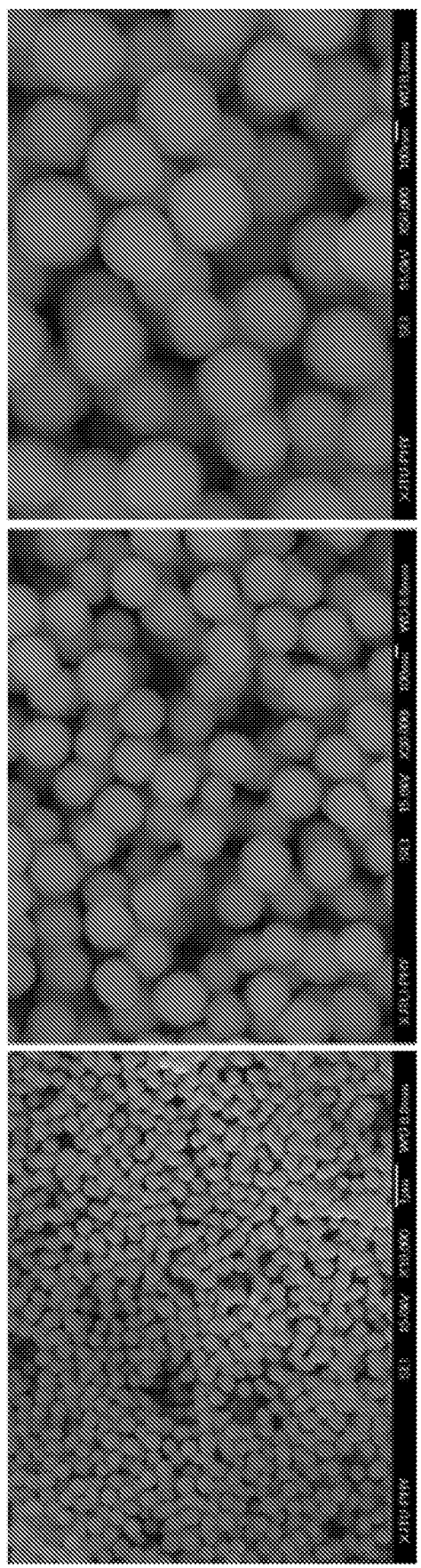
FIG. 11A
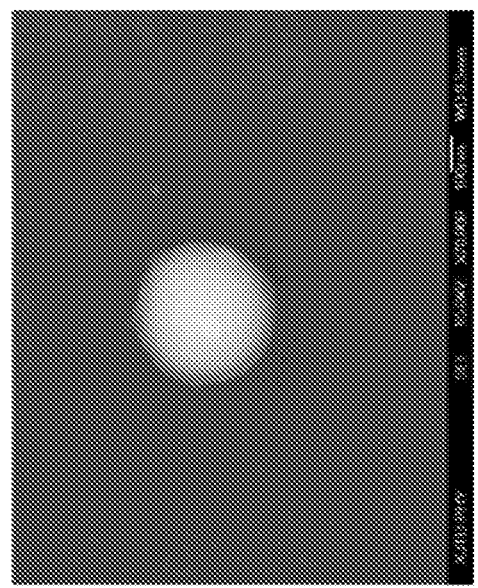
FIG. 11F
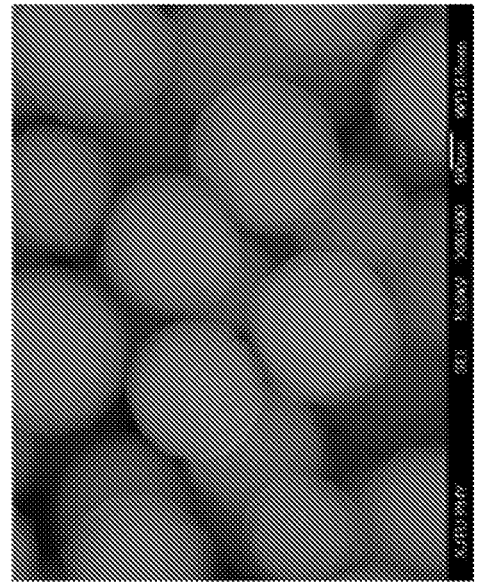
FIG. 11E
FIG. 11D

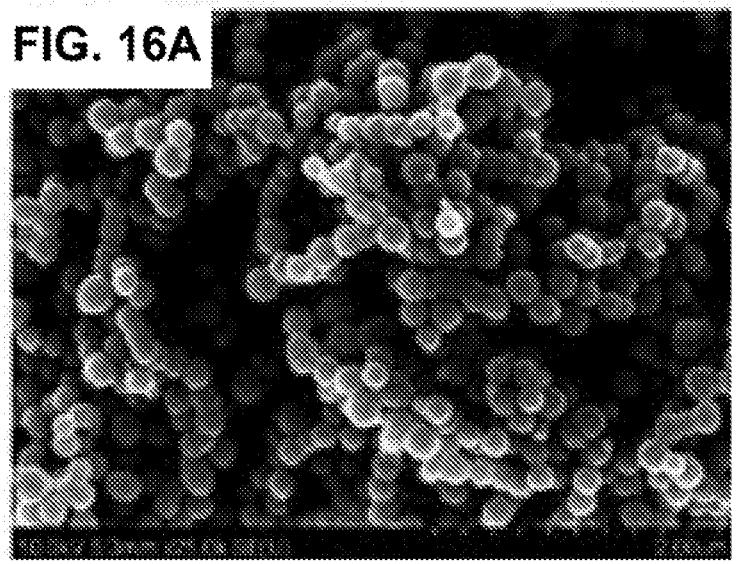
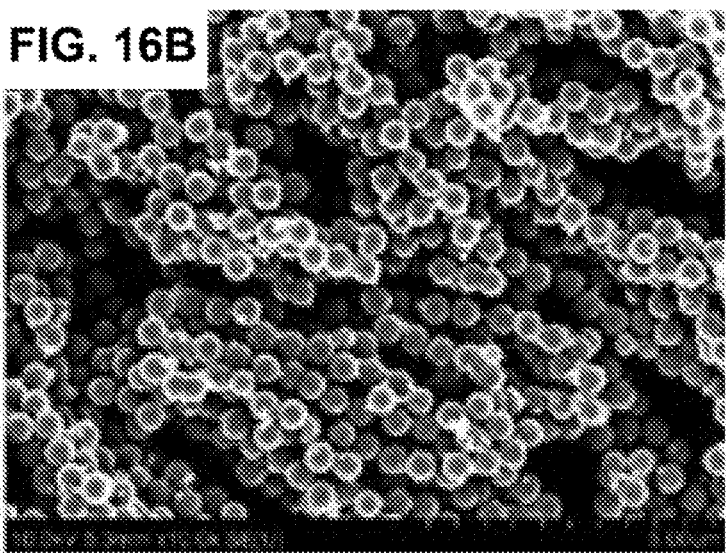

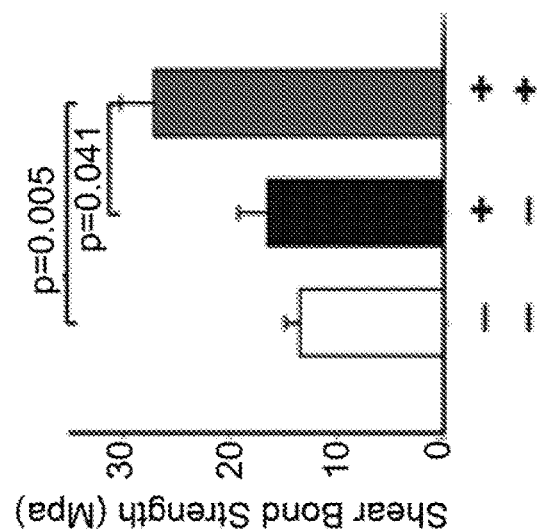
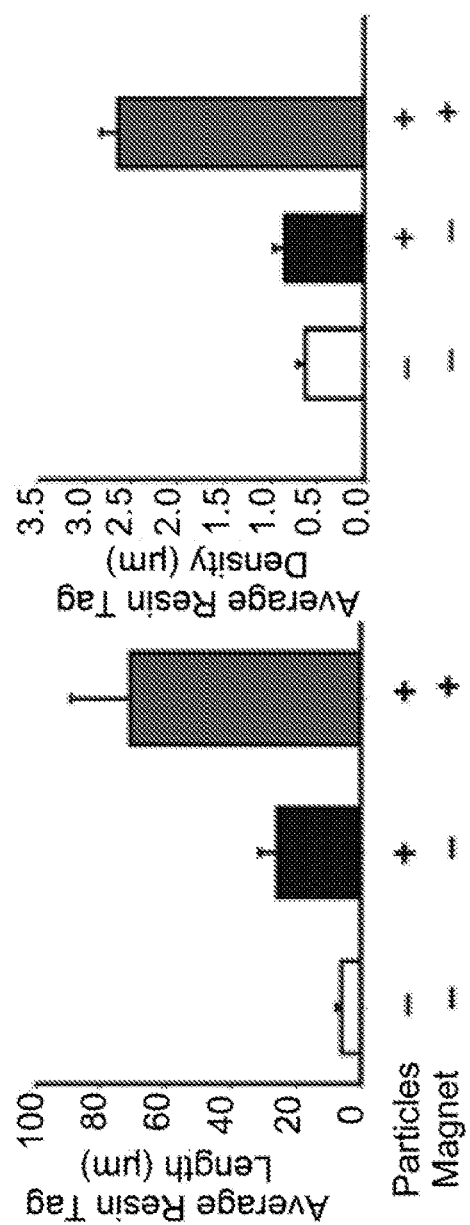
FIG. 19A  FIG. 19B  FIG. 19C

US 11,285,539 B2

SYNTHESIS AND FUNCTIONALIZATION OF HIGHLY MONODISPERSED IRON AND CORE/IRON OXIDE SHELL MAGNETIC PARTICLES WITH BROADLY TUNABLE DIAMETER

BACKGROUND OF THE INVENTION

Field of the Invention

Provided are methods for preparing iron nanoparticles and to iron nanoparticles produced by those methods. The invention also provides methods for coating the iron nanoparticles with oxides and functionalizing the iron nanoparticles with organic and polymeric ligands. Additionally, the invention provides methods of using such iron nanoparticles.

BRIEF SUMMARY OF THE INVENTION

The present invention provides a process for the preparation of iron nanoparticles, comprising reacting a $Fe^{2+}$ salt with a reducing agent in the presence of a polymer surfactant and a base.

In some embodiments, the $Fe^{2+}$ salt is $FeCl_2$, $FeBr_2$, $FeI_2$, or $Fe(SO_4)_2$.

In some embodiments, the reducing agent is $NaBH_4$, $LiBH_4$, $N_2H_4$, $NaH_2PO_3$, $NaBH_3CN$, $NaBH(OAc)_3$, a sulfite, or an amino acid.

In some embodiments, the polymer surfactant is polyvinylpyrrolidone (PVP), polyacrylic acid, polystyrene sulfonate, poly(allylamine hydrochloride), polyvinyl alcohol, poly(methacrylic acid), polyaspartic acid, polyallylamine hydrochloride, poly(2-acrylamido-2-methyl-1-propanesulfonic acid), polyacrylamide, polypeptides, glycosaminoglycans, Triton X-100, polyethylene glycol nonyl phenyl ether, or a deoxyribonucleic acid.

In some embodiments, the polymer surfactant is a PVP having a number average molecular weight of 1 to 80 kilodaltons. In one embodiment, the PVP has a number average molecular weight of about 40 kilodaltons.

In some embodiments, the base is aqueous NaOH or KOH.

In some embodiments, the reducing agent and base is added to the $Fe^{2+}$ salt and the polymer surfactant over 15 minutes to 24 hours in a batch process.

In some embodiments, the reducing agent and base is added to the $Fe^{2+}$ salt and the polymer surfactant with stirring. In some embodiments, the stirring rate is between 50 and 2000 rpm. In some embodiments, the stirring rate is greater than 500 rpm.

In some embodiments, the reducing agent and base is added to the $Fe^{2+}$ salt and the polymer surfactant in a continuous process.

In some embodiments, the reacting is carried out in aqueous solution.

In some embodiments, the concentration of polymer surfactant in water is 0.001 to 0.100 g/mL, the concentration of reducing agent is 0.01 to 1.0 M, and the concentration of base is 0.0001 to 1.0 M.

In one embodiment, the polymer surfactant is PVP of 40 kilodaltons having a concentration of about 0.03 g/mL, the reducing agent is $NaBH_4$ having a concentration of about 0.1M and the base is NaOH having a concentration of about 0.6 mM to about 1.3 mM.

In some embodiments, the iron nanoparticles have an average size of 50-1000 nm.

In some embodiments, the iron nanoparticles have an average size of about 210 nm, about 311 nm, about 400 nm, about 466 nm, about 530 nm, about 656 nm, or about 724 nm.

In some embodiments, the process further comprises isolating the iron nanoparticles.

In some embodiments, the iron nanoparticles are in the form of a precipitate.

In some embodiments, the iron nanoparticles are dispersed in an aqueous solution or ethanol and the aqueous solution is removed by decanting, centrifugation or filtration to give isolated iron nanoparticles.

In some embodiments, the isolated iron nanoparticles are washed with an alcohol or alternatively with alcohol and water. In one embodiment, the alcohol is ethanol.

In some embodiments, the iron nanoparticles further comprise a ligand on the iron nanoparticles.

In some embodiments, the ligand is an acrylate or a polymer.

In some embodiments, the iron nanoparticles further comprises at least one shell on the nanoparticles. In some embodiments, the at least one shell comprises a metal oxide. In one embodiment, the at least one shell comprises silica.

In some embodiments, the iron nanoparticles are embedded in a polymeric matrix. In one embodiment, the polymeric matrix comprises a polyacrylate.

In some embodiment, the iron nanoparticles are linked to a drug.

In some embodiments, provided is a method of treating a condition that responds to a drug, comprising administering an effective amount of the iron nanoparticles linked to the drug.

In some embodiments, the iron nanoparticles are part of a dental restoration.

In some embodiment, provided is a method of treating a condition that benefits from hyperthermia, comprising administering to an animal in need thereof the iron nanoparticles, exposing a portion of the animal to a magnetic field, thereby concentrating the iron nanoparticles to the portion exposed to the magnetic field, and exposing the portion of the animal to an excitation source, thereby exciting the iron nanoparticles and causing localized hyperthermia. In one embodiment, the condition is a tumor and the portion of the animal exposed to the magnetic field comprises the tumor.

BRIEF DESCRIPTION OF DRAWINGS

FIGS. 2A, 2C and 2E show a series of SEM images of the iron nanoparticles obtained under different reaction conditions at different concentrations of NaOH: NaOH 1.25 mM (FIGS. 2A and 2E); and NaOH 0.625 mM (FIG. 2C). FIGS. 2B, 2D, and 2F show a series of size distribution charts of the iron nanoparticles obtained under different reaction conditions at different concentrations of NaOH: NaOH 1.25 mM (FIGS. 2B and 2F); and NaOH 0.625 mM (FIG. 2D).

FIGS. 3A-3D show a series of SEM images of iron nanoparticles with different sizes: 724 nm (FIG. 3A), 656 nm (FIG. 3B), 466 nm (FIG. 3C), and 311 nm (FIG. 3D).

FIG. 8A before; and FIG. 8B after being placed in the presence of a magnet.

FIGS. 11A-11F are SEM images of iron nanoparticles with a size of about 300 nm after coating with a silica shell.

FIGS. 16A-16B are SEM images of iron nanoparticles with different sizes: 250 nm (FIG. 16A), and 500 nm (FIG. 16B).

FIG. 19A is a bar graph showing quantification of average resin tag length. FIG. 19B is a bar graph showing quantification of average resin tag density. FIG. 19C is a bar graph showing shear bond strength of teeth restored using the nanoparticle-doped adhesive system compared to that using the controls.

DETAILED DESCRIPTION OF THE INVENTION

Figure 1:
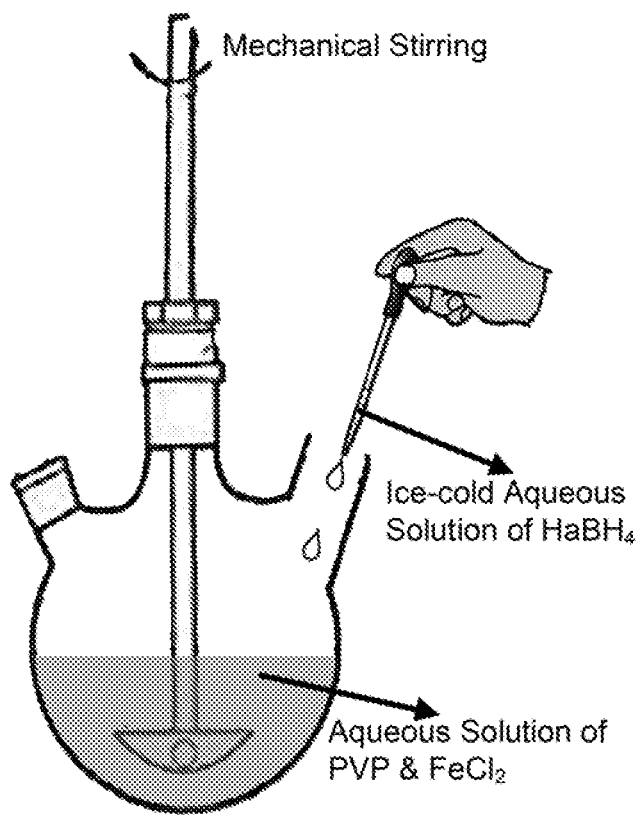
FIG. 1 depicts a scheme for a batch process for the preparation of iron nanoparticles.

The invention described herein are highly monodispersed iron and iron core/iron oxide shell magnetic particles with broadly tunable diameters (50-1000 nm range) and methods of making the same.

In one embodiments, provided is a process for the preparation of iron nanoparticles, comprising reacting a $Fe^{2+}$ salt with a reducing agent in the presence of a polymer surfactant and a base.

We have developed i) a synthetic method for the preparation of highly monodispersed iron and iron core/iron oxide shell magnetic particles through batch reaction and/or continuous microfluidic reaction, ii) a strategy for controlling the color of the magnetic particles, and iii) a protocol for the functionalization of such magnetic particles with polymerizable acrylate ligands. This approach is based on the fast reduction of iron ions in the presence of FDA-approved polymer surfactants. This method has the following unique merits: i) it allows for the precise control over the diameter of the particles in a range of 50-1000 nm; ii) It is scalable to produce large quantity of particles; iii) It is simple yet reproducible; iv) It is compatible with continuous synthesis in flow; and v) the particles are biocompatible. We further developed a synthetic route for the surface modification of magnetic particles with acrylate monomers. The acrylate-functionalized magnetic particles can be used for new generation of dental materials.

Due to their large magnetization and magnetostatic force, pure Fe particles have been widely used in magnetism and electricity, catalysis, labeling and magnetic separation of biological materials, MM contrast enhancement, hyperthermia treatment and drug delivery[1,2]. The properties of Fe particles are strongly dependent on their size and shape. There is a burgeoning literature about the synthesis of small Fe nanoparticles with diameter below about 20 nm using the thermal decomposition of iron pentacarbonyl[2,3]. However, there are only few reports on the preparation of monodispersed Fe particles over 100 nm. Three major methods are: (1) gas flow sputtering[1], (2) reduction of $Fe_2O_3$ or $Fe_3O_4$ by heating under CO or $H_2$ atmosphere[4-6], and (3) chemical reduction by $NaBH_4$[7,8]. However, the methods (1) and (2) are not cost-effective, and they offer limited control over the size and size distribution of particles. The method (3) mainly produces Fe particle chains. To date, there is no report on the synthesis of highly monodispersed spherical Fe nanoparticles with tunable diameter. Therefore, there is urgent to develop a simple, scalable yet inexpensive strategy for the synthesis method of Fe nanoparticles. We have recently developed i) a synthetic method for the preparation of highly monodispersed iron and iron core/iron oxide shell magnetic particles through batch reaction and/or continuous microfluidic reaction, ii) a strategy for controlling the color of the magnetic particles, and iii) a protocol for the functionalization of such magnetic particles with polymerizable acrylate ligands. The synthetic approach is based on the fast reduction of $Fe^{2+}$ ions in the presence of FDA-approved polymer surfactant (polyvinylpyrrolidone, PVP). This method has the following unique merits: i) it allows for the precise control over the diameter of the particles in a range of 50-1000 nm; ii) it is scalable to produce large quantity of particles; iii) it is simple yet reproducible; iv) it is compatible with continuous synthesis in flow; and v) the particles are biocompatible. We further developed a synthetic route for the surface modification of magnetic particles with acrylate monomers. The acrylate-functionalized magnetic particles can be used for new generation of dental materials.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a nanoparticle" includes a plurality of such nanoparticles, and the like.

The term "about," as used herein, includes the recited number ±10%. For example, "about 100 nm" encompasses a range of sizes from 90 nm to 110 nm.

The term "nanoparticles" as used herein refers to solid particles having a size of less than 1000 nm.

As used herein, the term "shell" refers to material deposited onto a nanoparticle core or onto previously deposited shells of the same or different composition and that result from a single act of deposition of the shell material.

A "ligand" is a molecule capable of interacting (whether weakly or strongly) with one or more faces of a nanostructure, e.g., through covalent, ionic, van der Waals, or other molecular interactions with the surface of the nanostructure.

Unless clearly indicated otherwise, ranges listed herein are inclusive.

A variety of additional terms are defined or otherwise characterized herein.

Process for Synthesizing Iron Nanoparticles

Provided is a process to prepare iron nanoparticles, comprising reacting a $Fe^{2+}$ salt with a reducing agent in the presence of a polymer surfactant and a base. In one embodiment, the $Fe^{2+}$ salt is $FeCl_2$, the reducing agent is $NaBH_4$, and the polymer surfactant is polyvinylpyrrolidone (PVP).

In some embodiments, the $Fe^{2+}$ salt is $FeCl_2$, $FeBr_2$, $FeI_2$, or $Fe(SO_4)_2$. In some embodiments, the $Fe^{2+}$ salt is $FeCl_2$.

In some embodiments, the reducing agents is $NaBH_4$, $LiBH_4$, $N_2H_4$, $NaH_2PO$, $NaBH_3CN$, $NaBH(OAc)_3$, a sulfite, or an amino acid. Examples of amino acids that may be used as a reducing agent include methionine and cysteine. Examples of sulfites that may be used as a reducing agent include sodium sulfite, sodium hydrogen sulfite, sodium metabisulfite, potassium metabisulfite, potassium sulfite, calcium sulfite, calcium hydrogen sulfite, potassium hydrogen sulfite. In some embodiments, the reducing agent is $NaBH_4$.

In some embodiments, the concentration of the reducing agent is about 0.01 M to 0.05 M, 0.01 M to 0.10 M, 0.01 M to 0.20 M, 0.01 M to 0.30 M, 0.01 M to 0.40 M, 0.01 M to 0.50 M, 0.01 M to 0.60 M, 0.01 M to 0.70 M, 0.01 M to 0.80 M, 0.01 M to 0.90 M, 0.01 M to 1.00 M, 0.05 M to 0.10 M, 0.05 M to 0.20 M, 0.05 M to 0.30 M, 0.05 M to 0.40 M, 0.05 M to 0.50 M, 0.05 M to 0.60 M, 0.05 M to 0.70 M, 0.05 M to 0.80 M, 0.05 M to 0.90 M, 0.05 M to 1.00 M, 0.10 M to 0.20 M, 0.10 M to 0.30 M, 0.10 M to 0.40 M, 0.10 M to 0.50 M, 0.10 M to 0.60 M, 0.10 M to 0.70 M, 0.10 M to 0.80 M, 0.10 M to 0.90 M, 0.10 M to 1.00 M, 0.20 M to 0.30 M, 0.20 M to 0.40 M, 0.20 M to 0.50 M, 0.20 M to 0.60 M, 0.20 M to 0.70 M, 0.20 M to 0.80 M, 0.20 M to 0.90 M, 0.20 M to 1.00 M, 0.30 M to 0.40 M, 0.30 M to 0.50 M, 0.30 M to 0.60 M, 0.30 M to 0.70 M, 0.30 M to 0.80 M, 0.30 M to 0.90 M, 0.30 M to 1.00 M, 0.40 M to 0.50 M, 0.40 M to 0.60 M, 0.40 M to 0.70 M, 0.40 M to 0.80 M, 0.40 M to 0.90 M, or 0.40 M to 1.00 M.

In some embodiments, the polymer surfactant is polyvinylpyrrolidone (PVP), polyacrylic acid, polystyrene sulfonate, poly(allylamine hydrochloride), polyvinyl alcohol, poly(methacrylic acid), polyaspartic acid, polyallylamine hydrochloride, poly(2-acrylamido-2-methyl-1-propanesulfonic acid), polyacrylamide, polypeptides, glycosaminoglycans, Triton X-100, polyethylene glycol nonyl phenyl ether, or a deoxyribonucleic acid. In some embodiments, the polymer surfactant is PVP.

In some embodiments, the number average molecular weight of PVP is 1 kilodalton to 5 kilodaltons, 1 kilodaltons to 10 kilodaltons, 1 kilodaltons to 20 kilodaltons, 1 kilodaltons to 30 kilodaltons, 1 kilodaltons to 40 kilodaltons, 1 kilodaltons to 50 kilodaltons, 1 kilodaltons to 60 kilodaltons, 1 kilodaltons to 70 kilodaltons, 1 kilodaltons to 80 kilodaltons, 1 kilodaltons to 90 kilodaltons, 1 kilodaltons to 100 kilodaltons, 5 kilodaltons to 10 kilodaltons, 5 kilodaltons to 20 kilodaltons, 5 kilodaltons to 30 kilodaltons, 5 kilodaltons to 40 kilodaltons, 5 kilodaltons to 50 kilodaltons, 5 kilodaltons to 60 kilodaltons, 5 kilodaltons to 70 kilodaltons, 5 kilodaltons to 80 kilodaltons, 5 kilodaltons to 90 kilodaltons, 5 kilodaltons to 100 kilodaltons, 10 kilodaltons to 20 kilodaltons, 10 kilodaltons to 30 kilodaltons, 10 kilodaltons to 40 kilodaltons, 10 kilodaltons to 50 kilodaltons, 10 kilodaltons to 60 kilodaltons, 10 kilodaltons to 70 kilodaltons, 10 kilodaltons to 80 kilodaltons, 10 kilodaltons to 90 kilodaltons, 10 kilodaltons to 100 kilodaltons, 20 kilodaltons to 30 kilodaltons, 20 kilodaltons to 40 kilodaltons, 20 kilodaltons to 50 kilodaltons, 20 kilodaltons to 60 kilodaltons, 20 kilodaltons to 70 kilodaltons, 20 kilodaltons to 80 kilodaltons, 20 kilodaltons to 90 kilodaltons, 20 kilodaltons to 100 kilodaltons, 30 kilodaltons to 40 kilodaltons, 30 kilodaltons to 50 kilodaltons, 30 kilodaltons to 60 kilodaltons, 30 kilodaltons to 70 kilodaltons, 30 kilodaltons to 80 kilodaltons, 30 kilodaltons to 90 kilodaltons, 30 kilodaltons to 100 kilodaltons, 40 kilodaltons to 50 kilodaltons, 40 kilodaltons to 60 kilodaltons, 40 kilodaltons to 70 kilodaltons, 40 kilodaltons to 80 kilodaltons, 40 kilodaltons to 90 kilodaltons, or 40 kilodaltons to 100 kilodaltons. In some embodiments, the number average molecular weight of PVP is 1 kilodalton to 80 kilodaltons.

In some embodiments, the number average molecular weight (kilodaltons) of PVP is about 1 kilodalton, about 5 kilodaltons, about 10 kilodaltons, about 20 kilodaltons, about 30 kilodaltons, about 40 kilodaltons, about 50 kilodaltons, about 60 kilodaltons, about 70 kilodaltons, about 80 kilodaltons, about 90 kilodaltons or about 100 kilodaltons. In some embodiments, the number average molecular weight (kilodaltons) of PVP is about 40 kilodaltons.

In some embodiments, the concentration of the PVP in water is 0.001 g/mL to 0.005 g/mL, 0.001 g/mL to 0.010 g/mL, 0.001 g/mL to 0.020 g/mL, 0.001 g/mL to 0.030 g/mL, 0.001 g/mL to 0.040 g/mL, 0.001 g/mL to 0.050 g/mL, 0.001 g/mL to 0.060 g/mL, 0.001 g/mL to 0.070 g/mL, 0.001 g/mL to 0.080 g/mL, 0.001 g/mL to 0.090 g/mL, 0.001 g/mL to 0.100 g/mL, 0.005 g/mL to 0.010 g/mL, 0.005 g/mL to 0.020 g/mL, 0.005 g/mL to 0.030 g/mL, 0.005 g/mL to 0.040 g/mL, 0.005 g/mL to 0.050 g/mL, 0.005 g/mL to 0.060 g/mL, 0.005 g/mL to 0.070 g/mL, 0.005 g/mL to 0.080 g/mL, 0.005 g/mL to 0.090 g/mL, 0.005 g/mL to 0.100 g/mL, 0.010 g/mL to 0.020 g/mL, 0.010 g/mL to 0.030 g/mL, 0.010 g/mL to 0.040 g/mL, 0.010 g/mL to 0.050 g/mL, 0.010 g/mL to 0.060 g/mL, 0.010 g/mL to 0.070 g/mL, 0.010 g/mL to 0.080 g/mL, 0.010 g/mL to 0.090 g/mL, 0.010 g/mL to 0.100 g/mL, 0.020 g/mL to 0.030 g/mL, 0.020 g/mL to 0.040 g/mL, 0.020 g/mL to 0.050 g/mL, 0.020 g/mL to 0.060 g/mL, 0.020 g/mL to 70.00 g/mL, 0.020 g/mL to 0.080 g/mL, 0.020 g/mL to 0.090 g/mL, 0.020 g/mL to 0.100 g/mL, 0.030 g/mL to 0.040 g/mL, 0.030 g/mL to 0.050 g/mL, 0.030 g/mL to 0.060 g/mL, 0.030 g/mL to 0.070 g/mL, 0.030 g/mL to 0.080 g/mL, 0.030 g/mL to 0.090 g/mL, 0.030 g/mL to 0.100 g/mL, 0.040 g/mL to 0.050 g/mL, 0.040 g/mL to 0.060 g/mL, 0.040 g/mL to 0.070 g/mL, 0.040 g/mL to 0.080 g/mL, 0.040 g/mL to 0.090 g/mL, or 0.040 g/mL to 0.100 g/mL.

Exemplary PVPs include those sold under the name PVP10 (Sigma-Aldrich), PVP40 (Sigma-Aldrich), PVP360 (Sigma-Aldrich), and under the trade name LUVITEC® (BASF Corporation), LUVICROSS® (BASF Corporation), COLLACRAL® VAL (BASF Corporation), Plasdone™ (Ashland Global Holdings Inc.), Kollidon® 25, Kollidon® 30 and Kollidon® 90 (BASF Corporation).

In some embodiments, the base is aqueous NaOH or KOH. In some embodiments, the base is NaOH.

In some embodiments, the concentration of the base is about 0.01 M to 0.05 M, 0.01 M to 0.10 M, 0.01 M to 0.20 M, 0.01 M to 0.30 M, 0.01 M to 0.40 M, 0.01 M to 0.50 M, 0.01 M to 0.60 M, 0.01 M to 0.70 M, 0.01 M to 0.80 M, 0.01 M to 0.90 M, 0.01 M to 1.00 M, 0.05 M to 0.10 M, 0.05 M to 0.20 M, 0.05 M to 0.30 M, 0.05 M to 0.40 M, 0.05 M to 0.50 M, 0.05 M to 0.60 M, 0.05 M to 0.70 M, 0.05 M to 0.80 M, 0.05 M to 0.90 M, 0.05 M to 1.00 M, 0.10 M to 0.20 M, 0.10 M to 0.30 M, 0.10 M to 0.40 M, 0.10 M to 0.50 M, 0.10 M to 0.60 M, 0.10 M to 0.70 M, 0.10 M to 0.80 M, 0.10 M to 0.90 M, 0.10 M to 1.00 M, 0.20 M to 0.30 M, 0.20 M to 0.40 M, 0.20 M to 0.50 M, 0.20 M to 0.60 M, 0.20 M to 0.70 M, 0.20 M to 0.80 M, 0.20 M to 0.90 M, 0.20 M to 1.00 M, 0.30 M to 0.40 M, 0.30 M to 0.50 M, 0.30 M to 0.60 M, 0.30 M to 0.70 M, 0.30 M to 0.80 M, 0.30 M to 0.90 M, 0.30 M to 1.00 M, 0.40 M to 0.50 M, 0.40 M to 0.60 M, 0.40 M to 0.70 M, 0.40 M to 0.80 M, 0.40 M to 0.90 M, or 0.40 M to 1.00 M.

In some embodiments, the concentration of NaOH or KOH is about 0.1 mM to about 0.2 mM, 0.1 mM to about 0.3 mM, 0.1 mM to about 0.4 mM, 0.1 mM to about 0.5 mM, 0.1 mM to about 0.6 mM, 0.1 mM to about 0.7 mM, 0.1 mM to about 0.8 mM, 0.1 mM to about 0.9 mM, 0.1 mM to about 1.0 mM, 0.1 mM to about 1.1 mM, 0.1 mM to about 1.2 mM, 0.1 mM to about 1.3 mM, 0.1 mM to about 1.4 mM, 0.1 mM to about 1.5 mM, 0.2 mM to about 0.3 mM, 0.2 mM to about 0.4 mM, 0.2 mM to about 0.5 mM, 0.2 mM to about 0.6 mM, 0.2 mM to about 0.7 mM, 0.2 mM to about 0.8 mM, 0.2 mM to about 0.9 mM, 0.2 mM to about 1.0 mM, 0.2 mM to about 1.1 mM, 0.2 mM to about 1.2 mM, 0.2 mM to about 1.3 mM, 0.2 mM to about 1.4 mM, 0.2 mM to about 1.5 mM, 0.3 mM to about 0.4 mM, 0.3 mM to about 0.5 mM, 0.3 mM to about 0.6 mM, 0.3 mM to about 0.7 mM, 0.3 mM to about 0.8 mM, 0.3 mM to about 0.9 mM, 0.3 mM to about 1.0 mM, 0.3 mM to about 1.1 mM, 0.3 mM to about 1.2 mM, 0.3 mM to about 1.3 mM, 0.3 mM to about 1.4 mM, 0.3 mM to about 1.5 mM, 0.4 mM to about 0.5 mM, 0.4 mM to about 0.6 mM, 0.4 mM to about 0.7 mM, 0.4 mM to about 0.8 mM, 0.4 mM to about 0.9 mM, 0.4 mM to about 1.0 mM, 0.4 mM to about 1.1 mM, 0.4 mM to about 1.2 mM, 0.4 mM to about 1.3 mM, 0.4 mM to about 1.4 mM, 0.4 mM to about 1.5 mM, 0.5 mM to about 0.6 mM, 0.5 mM to about 0.7 mM, 0.5 mM to about 0.8 mM, 0.5 mM to about 0.9 mM, 0.5 mM to about 1.0 mM, 0.5 mM to about 1.1 mM, 0.5 mM to about 1.2 mM, 0.5 mM to about 1.3 mM, 0.5 mM to about 1.4 mM, 0.5 mM to about 1.5 mM, 0.6 mM to about 0.7 mM, 0.6 mM to about 0.8 mM, 0.6 mM to about 0.9 mM, 0.6 mM to about 1.0 mM, 0.6 mM to about 1.1 mM, 0.6 mM to about 1.2 mM, 0.6 mM to about 1.3 mM, 0.6 mM to about 1.4 mM, 0.6 mM to about 1.5 mM, 0.7 mM to about 0.8 mM, 0.7 mM to about 0.9 mM, 0.7 mM to about 1.0 mM, 0.7 mM to about 1.1 mM, 0.7 mM to about 1.2 mM, 0.7 mM to about 1.3 mM, 0.7 mM to about 1.4 mM, 0.7 mM to about 1.5 mM.

In some embodiments, the concentration of NaOH or KOH is about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, or about 1.5 mM.

In some embodiments, the reducing agent and the base are added to the $Fe^{2+}$ salt and the polymer surfactant over 15 minutes to 24 hours, over 15 minutes to 20 hours, over 15 minutes to 15 hours, over 15 minutes to 10 hours, over 15 minutes to 5 hours, over 15 minutes to 1 hour, over 15 minutes to 30 minutes, over 30 minutes to 24 hours, over 30 minutes to 20 hours, over 30 minutes to 15 hours, over 30 minutes to 10 hours, over 30 minutes to 5 hours, over 30 minutes to 1 hour, over 1 hour to 24 hours, over 1 hour to 20 hours, over 1 hour to 15 hours, over 1 hour to 10 hours, over 1 hour to 5 hours, over 5 hours to 24 hours, over 5 hours to 20 hours, over 5 hours to 15 hours, over 5 hours to 10 hours, over 10 hours to 24 hours, over 10 hours to 20 hours, over 10 hours to 15 hours, over 15 hours to 24 hours, over 15 hours to 20 hours, or over 20 hours to 24 hours.

In one embodiment, the reducing agent and the base is added to the $Fe^{2+}$ salt and polymer surfactant with stirring in a batch process as depicted in FIG. 1.

In some embodiments, the stirring rate is between 50 rpm and 2,000 rpm, between 50 rpm and 1,750 rpm, between 50 rpm and 1,500 rpm, between 50 rpm and 1,250 rpm, between 50 rpm and 1,000 rpm, between 50 rpm and 750 rpm, between 50 rpm and 500 rpm, between 50 rpm and 100 rpm, between 100 rpm and 2,000 rpm, between 100 rpm and 1,750 rpm, between 100 rpm and 1,500 rpm, between 100 rpm and 1,250 rpm, between 100 rpm and 1,000 rpm, between 100 rpm and 750 rpm, between 100 rpm and 500 rpm, between 500 rpm and 2,000 rpm, between 500 rpm and 1,750 rpm, between 500 rpm and 1,500 rpm, between 500 rpm and 1,250 rpm, between 500 rpm and 1,000 rpm, between 500 rpm and 750 rpm, between 750 rpm and 2,000 rpm, between 750 rpm and 1,750 rpm, between 750 rpm and 1,500 rpm, between 750 rpm and 1,250 rpm, between 750 rpm and 1,000 rpm, between 1,000 rpm and 2,000 rpm, between 1000 rpm and 1,750 rpm, between 1,000 rpm and 1,500 rpm, between 1,000 rpm and 1,250 rpm, between 1,250 rpm and 2,000 rpm, between 1,250 rpm and 1,750 rpm, between 1,250 rpm and 1,500 rpm, between 1,500 rpm and 2,000 rpm, or between 1,500 rpm and 1,750 rpm.

In some embodiments, the stirring rate is greater than 500 rpm.

In some embodiments, the reducing agent and the base is added to the Fe$^{2+}$ salt and the polymer surfactant in a continuous process. In one embodiment, a mixture of the reducing agent and the base is filled in a syringe. The mixture solution is slowly introduced into the reaction system by using a syringe pump. In another embodiment, two syringes that contain the reducing agent and the base separately are used for continuous injection of reactants.

In some embodiments, the process comprises using a continuous microreactor to synthesize the magnetic nanoparticles. In one embodiment, a mixture of reducing agents is filled in one syringe; and a mixture of Fe$^{2+}$ salt and polymer surfactant is filled in another syringe. Then the two liquids are simultaneously injected into a channel or a tubing and mixed in the channel or the tubing to react. The final product is collected at the end of the channel or the tubing.

In some embodiments, the sizes of iron nanoparticles are tuned by controlling the concentration and ratio of chemicals, for example, base, reducing agent, and polymer surfactant, and the additional rate of chemicals. In some embodiments, the sizes of iron nanoparticles are tuned by controlling the concentration of base, e.g., NaOH or KOH. The size of iron nanoparticles increases with a decrease of the concentration of NaOH.

In some embodiments, the sizes of iron nanoparticles are tuned by changing the solvent of the reaction, e.g., using water or ethanol mixture as solvent.

The size of the iron nanoparticles were determined by measuring their average diameter.

In some embodiments, the nanoparticles have an average diameter of 1000 nanometers or less. In some embodiments, the iron nanoparticles may have an average diameter of 1000 nanometers or less. In some embodiments, the diameter of the nanoparticle is between about 50 nm and about 1000 nm, between about 50 nm and about 800 nm, between about 50 nm and about 600 nm, between about 50 nm and about 400 nm, between about 50 nm and about 200 nm, between about 50 nm and about 100 nm, between about 100 nm and about 1000 nm, between about 100 nm and about 800 nm, between about 100 nm and about 600 nm, between about 100 nm and about 400 nm, between about 100 nm and about 200 nm, between about 200 nm and about 1000 nm, between about 200 nm and about 800 nm, between about 200 nm and about 600 nm, between about 200 nm and about 400 nm, between about 400 nm and about 1000 nm, between about 400 nm and about 800 nm, between about 400 nm and about 600 nm, between about 600 nm and about 1000 nm, between about 600 nm and about 800 nm, or between about 800 nm and about 1000 nm. In some embodiments, the average diameter of the nanoparticle is about 210 nm. In some embodiments, the average diameter of the nanoparticle is about 400 nm. In some embodiments, the average diameter of the nanoparticle is about 530 nm.

In some embodiments, the iron nanoparticles are in the form of a precipitate. In some process, the iron nanoparticles are in an aqueous solution and the solution is removed by decanting, centrifugation or filtration to isolate the iron nanoparticles. In another embodiment, the iron nanoparticles are concentrated by placing in the vicinity of a magnet and the solution is decanted.

In some embodiments, the iron nanoparticles are washed with a solvent. In some embodiments, the solvent is water, an alcohol, hexane, toluene, benzene, chloroform, or a mixture thereof. In one embodiment, the solvent is ethanol.

Shells

In some embodiments, the iron nanoparticles comprise at least one shell on the iron nanoparticles. Suitable shell materials include, but are not limited to, silica, alumina, titanium dioxide, zirconium dioxide, copper oxide, silver oxide, and the like. In some embodiments, the at least one shell comprises a metal oxide. In one embodiment, the at least one shell comprises iron oxide. In one embodiment, the at least one shell comprises silica. Exemplary synthesis of metal oxide shell and core/shell nanostructures is disclosed in U.S. Pat. Nos. 9,390,845, 8,343,627, and U.S. Patent No. US20120012778 A1.

In some embodiments, the shell has a thickness in the range from about 2 nm to about 100 nm, from about 2 nm to about 80 nm, from about 2 nm to about 60 nm, from about 2 nm to about 40 nm, from about 2 nm to about 20 nm, from about 2 nm to about 10 nm, from about 2 nm to about 5 nm, from about 5 nm to about 100 nm, from about 5 nm to about 80 nm, from about 5 nm to about 60 nm, from about 5 nm to about 40 nm, from about 5 nm to about 20 nm, from about 5 nm to about 10 nm, from about 10 nm to about 100 nm, from about 10 nm to about 80 nm, from about 10 nm to about 60 nm, from about 10 nm to about 40 nm, from about 10 nm to about 20 nm, from about 20 nm to about 100 nm, from about 20 nm to about 80 nm, from about 20 nm to about 60 nm, from about 20 nm to about 40 nm, from about 40 nm to about 100 nm, from about 40 nm to about 80 nm, from about 40 nm to about 60 nm, from about 60 nm to about 100 nm, from about 60 nm to about 80 nm, or from about 80 nm to about 100 nm.

Surface Functionalization

To modify the surface chemistry of the iron nanoparticles, a broad range of organic ligands with varying functional groups can be used to coat the surface of the iron nanoparticles or through an intermediate layer of oxide(s).

Examples of organic ligands for the iron nanoparticles include, but not limited to, alkane, alkene, alkyne, ketone, ether, nitrile, alcohol, polyol, polyethylene glycol, polypropylene glycol, amide, polyvinylpyrolidone, polyacrylate, polymethacryate, polyacrylic acid, ester, polyester, primary amine, secondary amine, tertiary amine, polyamine, sulfate, sulfonate, sulfonic acid, phosphate, phosphonate, phosphonic acid, fluorinated compounds (e.g., perfluoropolyether, fluoroalkane, ionic fluorocompounds, polyethylene glycol functionalized fluorocompounds), silicones, reactive silane groups (e.g., alkoxysilane), carboxylic acid, quaternary ammonium, phosphonium, zwitterion (e.g., phosphoryl choline, amino acids, and amino-sulfonic acid based compounds), aldehyde, surfactants, peptides, and nucleic acids.

In some embodiments, the iron nanoparticles are embedded in a polymeric matrix comprising the organic ligands described above. In some embodiment, the polymeric matrix comprises a polyacrylate.

Uses

In some embodiments, the iron nanoparticles can be used for drug delivery. In some embodiments, the iron nanoparticles are linked to a wide variety of ligands, including but not limited to, antibodies, antibody fragments, peptides, small molecules, polysaccharides, nucleic acids, aptamers, peptidomimetics, other mimetics and drugs alone or in combination. The ligands may be attached covalently (direct-conjugation) or noncovalently (indirect conjugation) to the nanoparticle surface. In some embodiments, the iron nanoparticles are linked to a drug. In some embodiments, the drug can be encapsulated in the coated structure. See U.S. Pat. Nos. 7,459,145 and 6,676,963 for methods of using nanoparticles in drug delivery.

Provided is a method of treating a condition that responds to a drug, comprising administering an effective amount of the iron nanoparticles linked to the drug.

In some embodiments, iron nanoparticles with ceramic oxide shells can be used to prepare ceramic mouldings for dental restoration. In some embodiments, the ceramic mouldings may be prepared by forming a suspension comprising iron nanoparticles with ceramic oxide shell, a polyreactive binder, an organic component, and additives; preparing a green body by curing the suspension by local introduction of radiation energy with formation of the geometric shape of the green body; subjecting the green body to a heat treatment to remove the binder to obtain a white body, and sintering the white body. See U.S. Patent Pub. No. US 2010/0025874 A1 for more details about preparing ceramic mouldings. In some embodiments, the ceramic oxide includes, but is not limited to, zirconium dioxide, aluminum oxide, barium oxide, and zinc oxide.

In some embodiments, provided is an adhesive resin doped with the iron nanoparticles. In some embodiments, the adhesive resin is a dental adhesive.

In some embodiments, the iron nanoparticle can be used to treat a condition that benefits from hyperthermia. In some embodiments, the treatment comprises administering the iron nanoparticles to an animal in need thereof; exposing a portion of the animal to a magnetic field, thereby concentrating the iron nanoparticles to the portion exposed to the magnetic field; and exposing the portion of the animal to an excitation source, thereby causing excitation of the iron nanoparticles and localized hypothermia. In some embodiments, the excitation source is light. In some embodiments, the excitation source is laser light. The induced localized hyperthermia can be used to repair tissue, e.g., joining tissue with other tissue or tissue with non-tissue material. See U.S. Pat. No. 6,685,730 for more details about treating various conditions involving hyperthermia treatment using nanoparticles.

In some embodiments, the condition is a tumor and the portion of the animal exposed to the magnetic field comprises the tumor.

EXAMPLES

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

Example 1

Synthesis of Iron Nanoparticles

A general method to synthesize monodispersed iron nanoparticles is described here. The synthesis scheme of FIG. 1 illustrates one method. An aqueous solution of PVP and $FeCl_2$ is placed in a three-neck flask. After being bubbled with argon (or nitrogen gas) to remove oxygen dissolved in the solution, an ice-cold aqueous solution of $NaBH_4$ and NaOH mixture is drop-wise added into the reaction using glass pipette (or slowly added into the reaction using syringe pump) under mechanical stirring. After completion of the reaction, iron nanoparticles are separated from the reaction by magnetic pulling using a magnetic bar. The iron nanoparticles are washed alternatively with water and ethanol to remove surfactants and/or unreacted precursors. The final product is stored in ethanol for future use.

General synthetic protocol for iron nanoparticles: All the chemicals were used directly without further treatment. The iron nanoparticles were prepared by a chemical reduction of $Fe^{2+}$ ions in the presence of PVP surfactant. $NaBH_4$ was used as the reducing agent and $FeCl_2$ was used as the source of Fe. The sizes of the iron nanoparticles were tuned by controlling the concentration of chemicals and the additional rate of chemicals. In a typical synthesis, a predetermined amount of $FeCl_2$ and 1 g PVP ($M_w$=40,000) were mixed in 30 ml $H_2O$. A 45 mL solution of $NaBH_4$ (0.1 M) and NaOH (1.25 mM) were added slowly into the above solution under vigorous mechanical stirring (>500 rpm). After the reaction proceeded for 20 minutes, the black precipitates were washed with ethanol several times and kept in ethanol.

Example 2

Tuning the Sizes of Iron Nanoparticles

Materials: Iron (II) chloride tetrahydrate (≥99%), 3-mercaptopropyl trimethoxysilane (KH570, 95%), Tetraethyl orthosilicate (TEOS, ≥99%), sodium borohydride (99%), polyvinylpyrrolidone (Mw 40,000), sodium hydroxide (≥99%), ammonium hydroxide solution (28% $NH_3$ in $H_2O$, ≥99.99%) were purchased from Aldrich and used as received. Deionized water was used for the preparation of all the aqueous solutions.

Synthetic protocol for iron nanoparticles with controlled size: Highly monodisperse iron nanoparticles with controlled size were prepared by a chemical reduction of $Fe^{2+}$ ions in the presence of PVP surfactant. $NaBH_4$ was used as the reducing agent and $FeCl_2$ was used as the source of Fe. The sizes of iron nanoparticles were tuned by controlling the concentration and the additional rate of chemicals or by varying the solvent composition for the reaction such as the ratio of ethanol to water solvent for the reaction. In a typical synthesis of iron nanoparticles with a size of about 530 nm, 1.00 g polyvinylpyrrolidone (PVP, $M_w$=40,000) was added into a 30.0 ml aqueous solution of Iron (II) chloride tetrahydrate (0.025 M) in a beaker. The solution was sonicated for 15 minutes to dissolve PVP and a homogeneous solution (called Solution A) was obtained. In another beaker, a 45.0 mL ice-cold sodium borohydride (0.100 M) aqueous solution and a 0.28 ml ice-cold sodium hydroxide NaOH (0.100 M) aqueous solution were mixed to produce a Solution B (ice-cold). The Solution A was transferred into a round bottom flask with three necks (Scheme 1). The solution was bubbled with argon (or nitrogen gas) to remove oxygen dissolved in the solution. Under vigorous mechanical stirring (560 rpm), Solution B was dropwise added into Solution A slowly using a glass pipette or slowly added into the reaction using a syringe pump under mechanical stirring. Solution B was kept in an ice-cold bath during the addition process. After completion of the reaction, the iron nanoparticles were separated from the reaction by magnetic pulling using a magnetic bar. The iron nanoparticles were washed alternatively with water and ethanol to remove surfactants and/or unreacted precursors. The precipitates were washed with ethanol for 5 times to remove PVP and the iron nanoparticles were stored in ethanol for further use.

FIGS. 2A, 2C, and 2E show representative SEM images of these products obtained at different concentrations of NaOH and addition rate of precursors. FIGS. 2B, 2D, and 2F show the representative size distributions of these products obtained at different concentrations of NaOH and addition rate of precursors. All the three samples contained magnetic particles with uniform sizes. When the concentration of NaOH was 1.25 mM, iron nanoparticles with an average diameter of 215±27 nm were produced (FIG. 2A and FIG. 2B). The size of iron nanoparticles increased with the decrease in the concentration of NaOH. Iron nanoparticles with an average size of 535±25 nm were synthesized when the concentration of NaOH was reduced to 0.625 mM (FIG. 2C and FIG. 2D). The quality of iron nanoparticles was further improved by controlling the addition rate of reductant. As shown in FIG. 2E and FIG. 2F, the morphology of iron nanoparticles (~400±23 nm in diameter) was further enhanced when the addition rate of reductant was optimized. This can be ascribed to the control over the nucleation rate of iron nanoparticles at the initial stage.

Figure 4A:
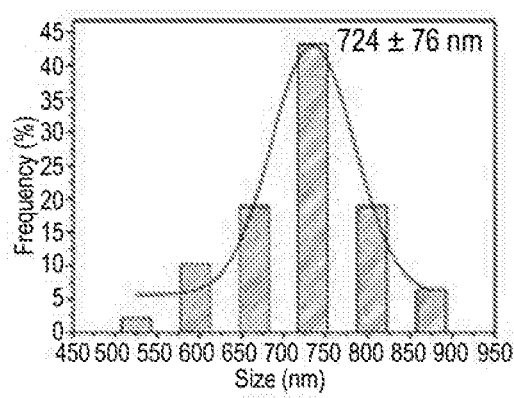
FIGS. 4A-4D are a series of bar graphs of size distribution of the iron nanoparticles with different sizes: 724 nm (FIG. 4A), 656 nm (FIG. 4B), 466 nm (FIG. 4C), and 311 nm (FIG. 4D).
Figure 4B:
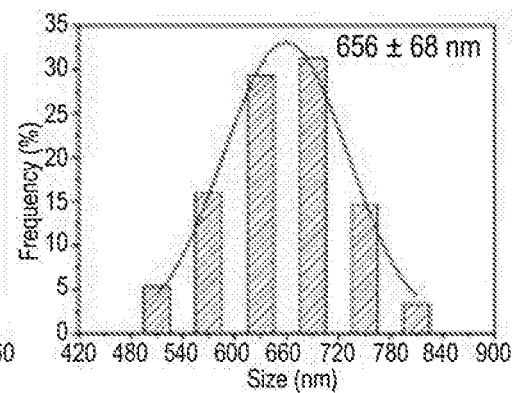
Figure 4C:
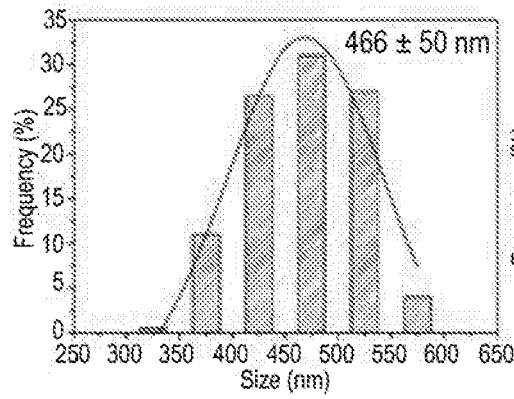
Figure 4D:
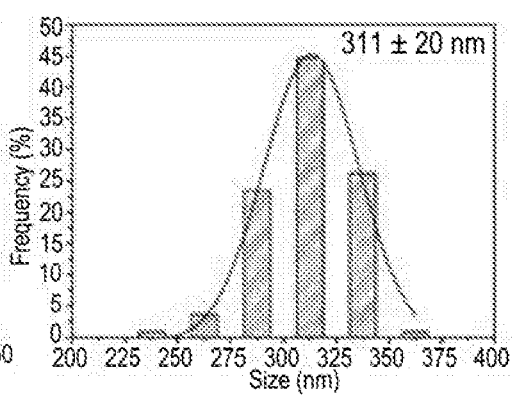

FIGS. 3A-3D shows representative SEM images of iron nanoparticles with different nanoparticle sizes obtained at different ratios of ethanol to water solvent: 724 nm (FIG. 3A), 656 nm (FIG. 3B), 466 nm (FIG. 3C), and 311 nm (FIG. 3D). FIGS. 4A-4D shows histograms of size distribution of the iron nanoparticles with different sizes obtained at different ratios of ethanol to water solvent: 724 nm (FIG. 4A), 656 nm (FIG. 4B), 466 nm (FIG. 4C), and 311 nm (FIG. 4D). The size of iron nanoparticles decreased gradually with the increase in the weight ratio of ethanol in the mixed solvent of ethanol and water. The resulting iron nanoparticles were highly monodispersed and were well-dispersed in polar solvents such as water and ethanol.

In summary, monodispersed iron nanoparticles were prepared by chemical reduction of $Fe^{2+}$ ions in the presence of PVP in aqueous solution and by using $NaBH_4$ as reducing agent. The sizes of monodispersed iron nanoparticles can be tuned in the range of 50 nm to 1000 nm by controlling reaction conditions.

Example 3

Characterization of the Iron Nanoparticles

X-ray powder diffraction (XRD) (FIGS. 5A-5B), Differential scanning calorimetry (DSC) (FIG. 6) and Hysteresis loops (FIGS. 7A-7D) characterization were also performed on the iron nanoparticles.

Figure 5A:
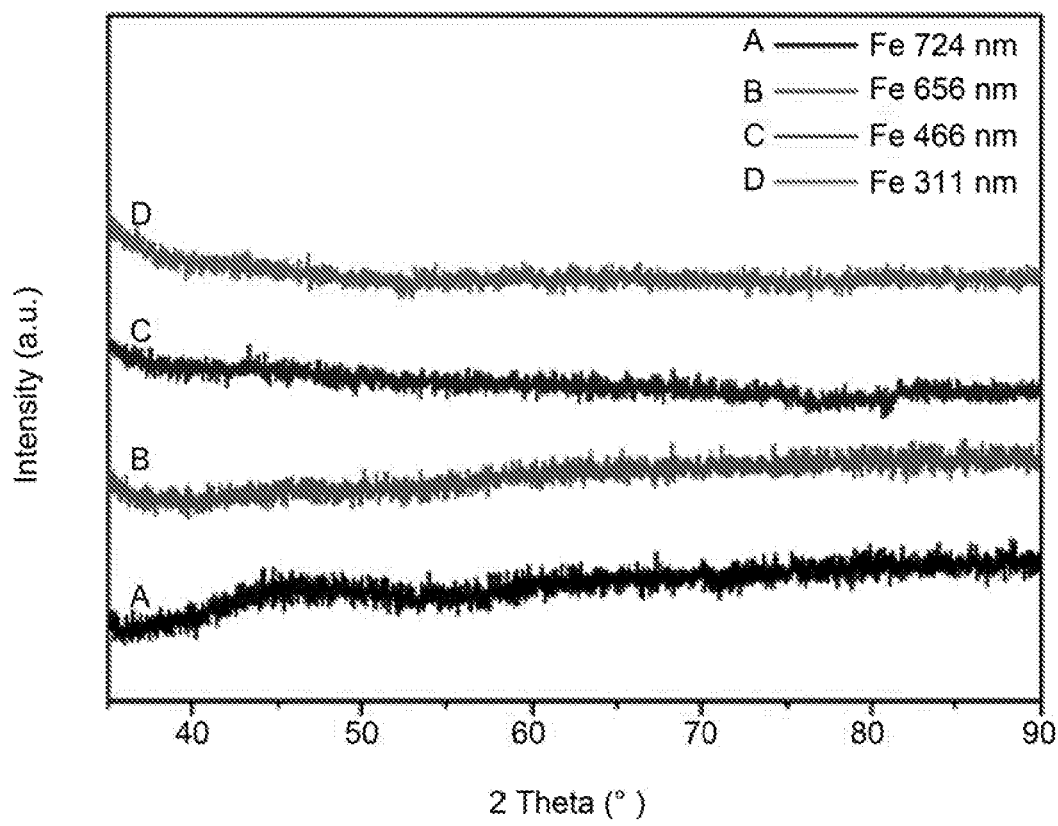
FIGS. 5A-5B are line graphs showing the intensity versus 2 Theta (°) of the X-ray powder diffraction (XRD) pattern of iron nanoparticles with different sizes before (FIG. 5A) and after (FIG. 5B) annealing at 600° C. for 3 hours under $N_2$ environment.
Figure 5B:
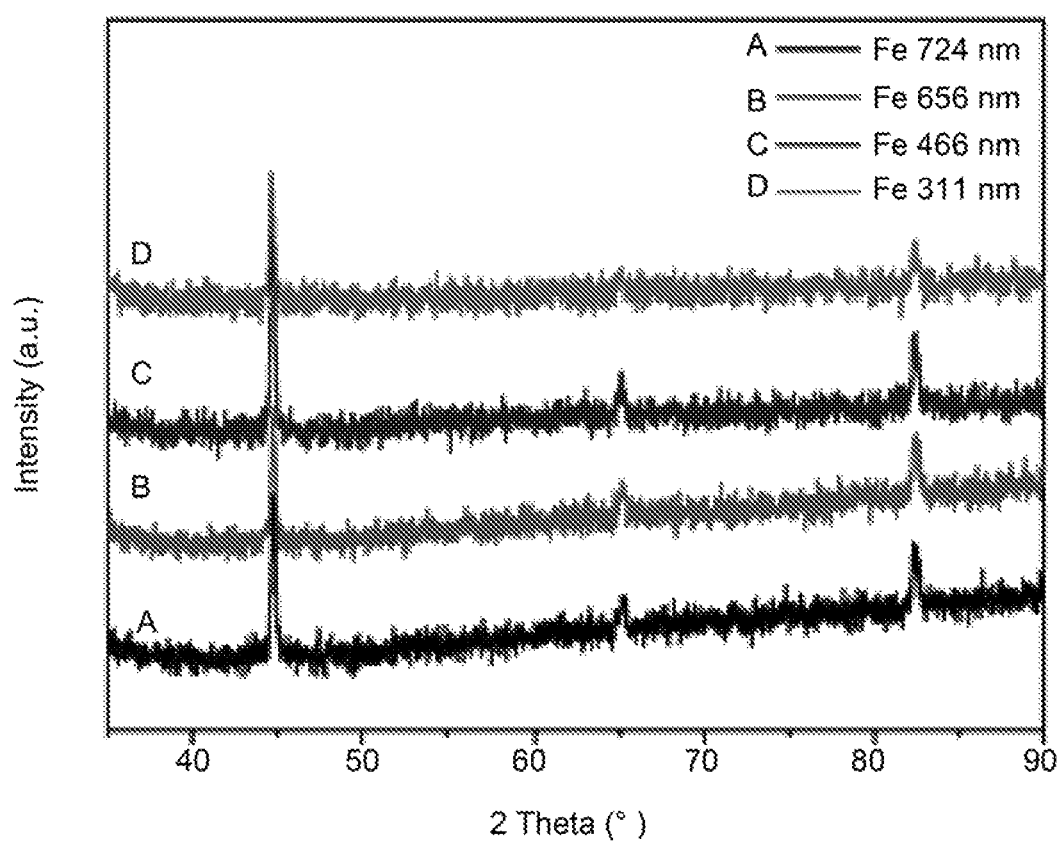

The as-synthesized iron nanoparticles are amorphous, as shown in the XRD measurement (FIG. 5A). Iron nanoparticles with high crystallinity can be obtained by annealing the nanoparticles at elevated temperature (e.g., 600° C.) for 3 hours under the protection of nitrogen (FIG. 5B).

Figure 6:
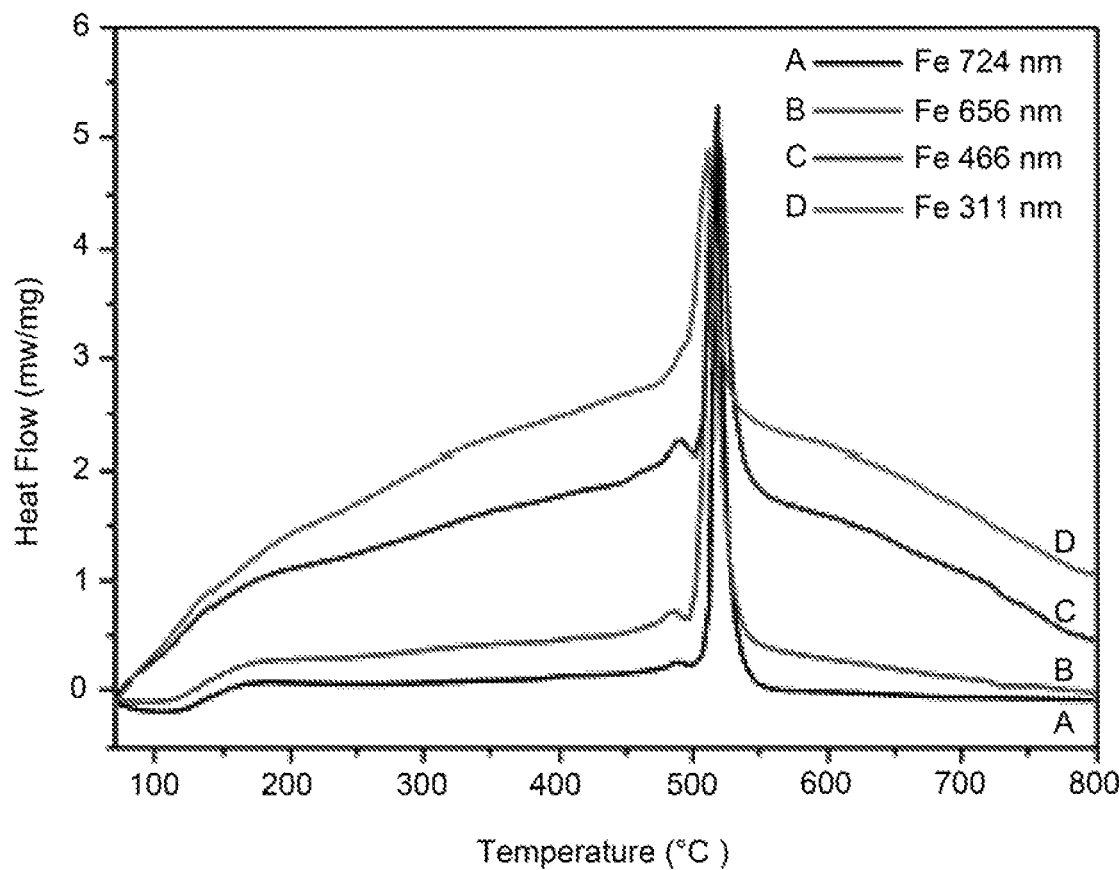
FIG. 6 is a line graph showing differential scanning calorimetry (DSC) curves of iron nanoparticles with different sizes.
Figure 7A:
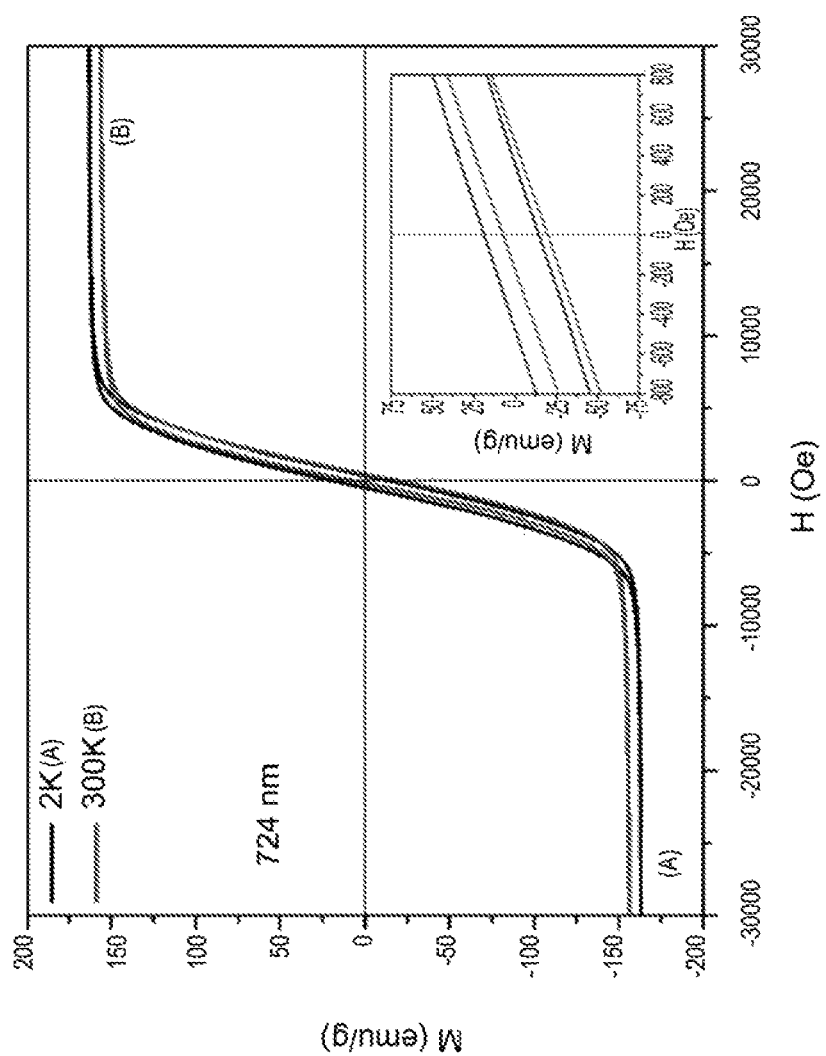
FIGS. 7A-7D are line graphs showing hysteresis loops of iron nanoparticles with different sizes at temperature of 2K and 300K under a field of 30000 Oe. The inset is a graph showing M-H loops for the same nanoparticle but under a field of 800 Oe.
Figure 7B:
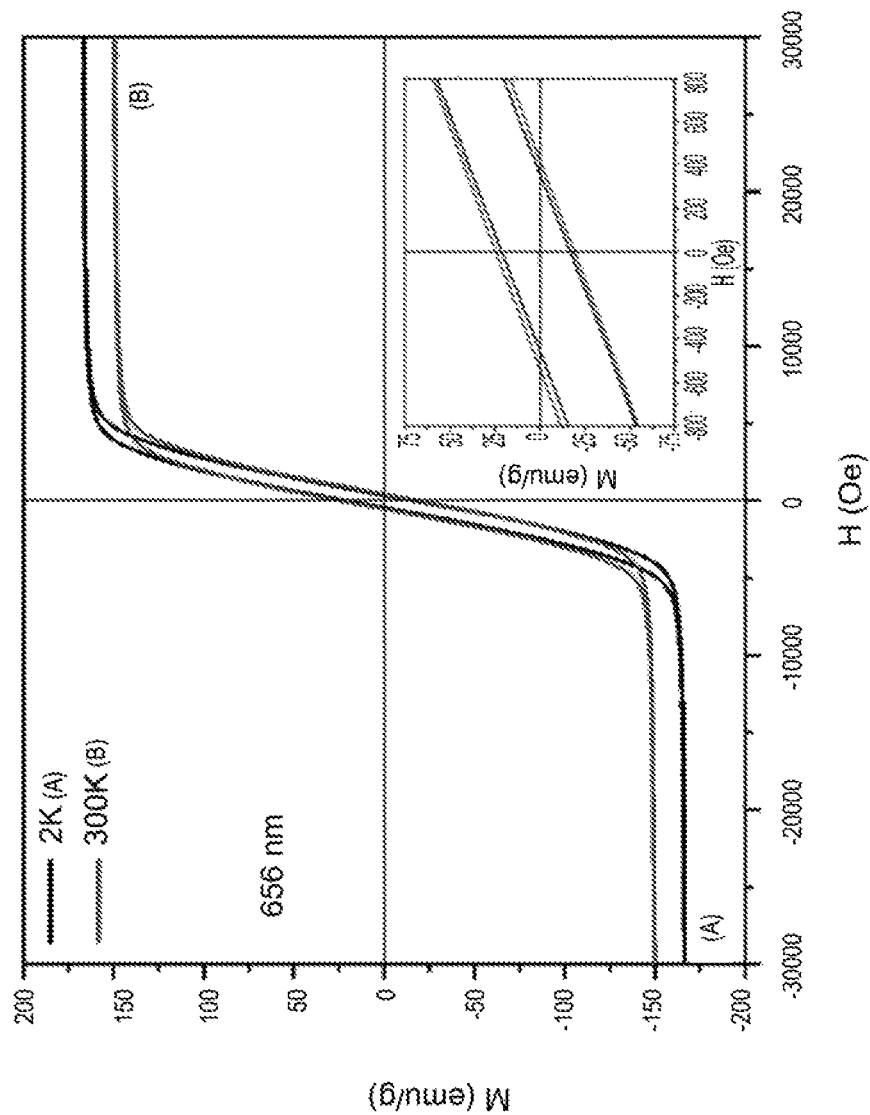
Figure 7C:
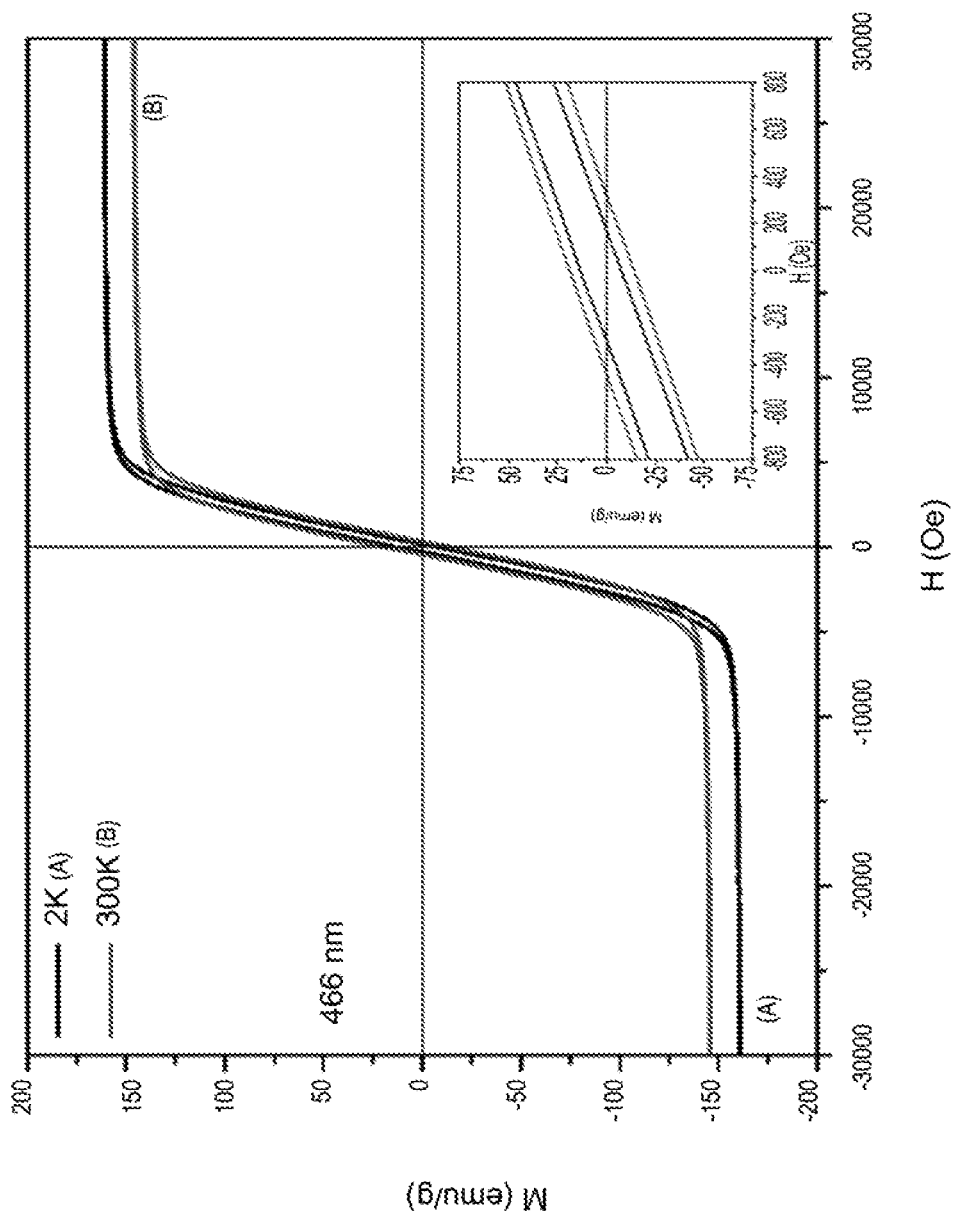
Figure 7D:
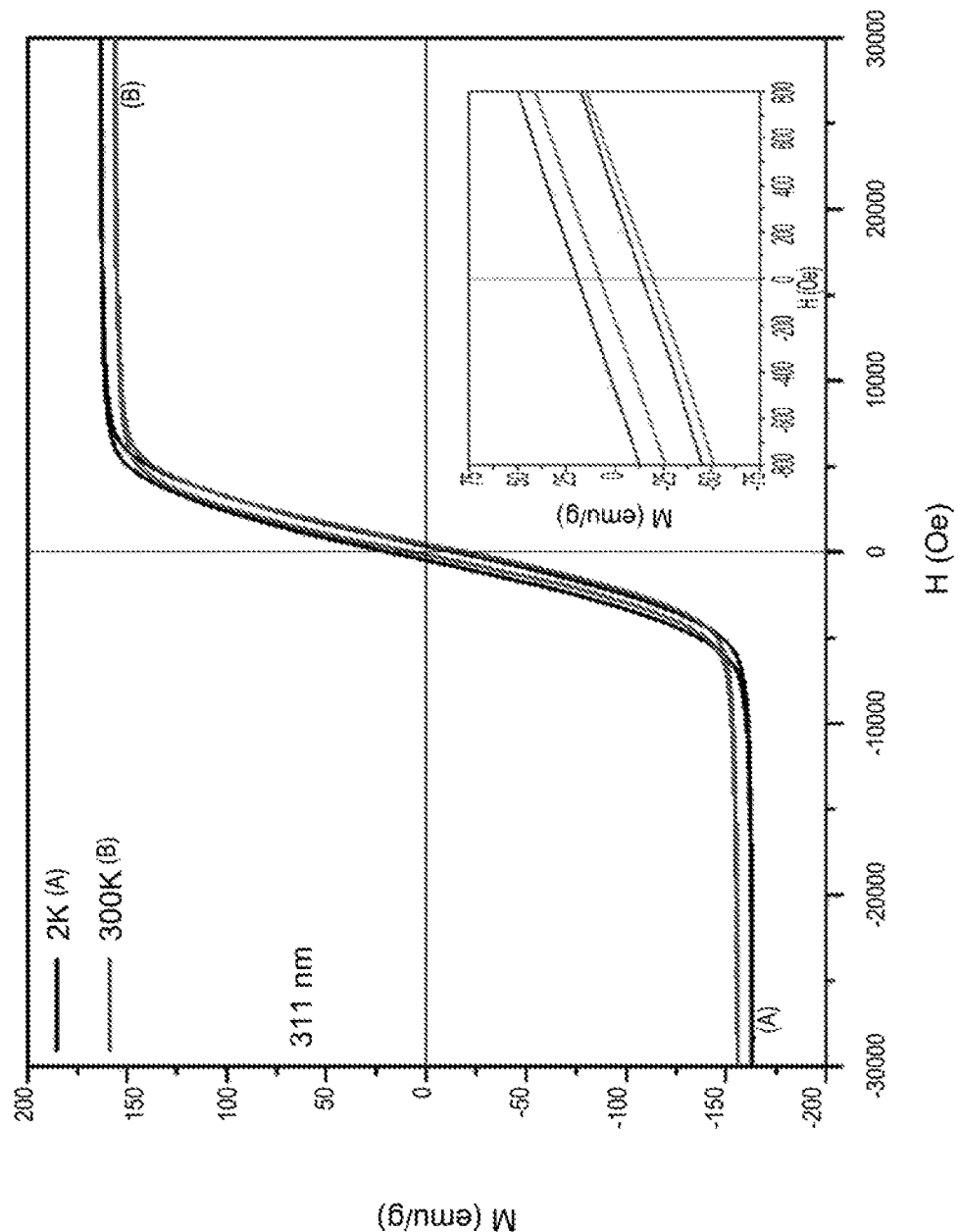

DSC was used to measure the crystallization point of amorphous iron nanoparticles. Thermal data were measured at a heating rate of 15° C. min' under the protection of nitrogen. As shown in FIG. 6, the crystallization temperature of amorphous iron nanoparticles was around 515° C., which was determined by the maximum heat flow peak.

The magnetic properties of iron nanoparticles were characterized by measuring the magnetization of these particles as a function of magnetic field. As shown in FIGS. 7A-7D, the magnetization of the iron nanoparticles is as high as 150 emu/g, which is significantly higher than that of iron oxide nanoparticles (usually below 100 emu/g). Hysteresis loops also indicated that the iron nanoparticles do not retain the magnetic properties when the external field is removed.

Figure 8A:
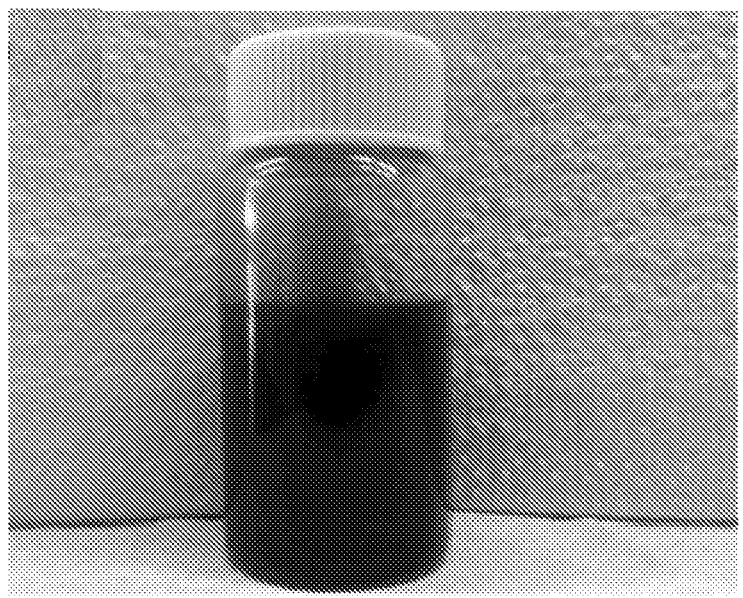
FIGS. 8A-8B are photographs of the iron nanoparticles.
Figure 8B:
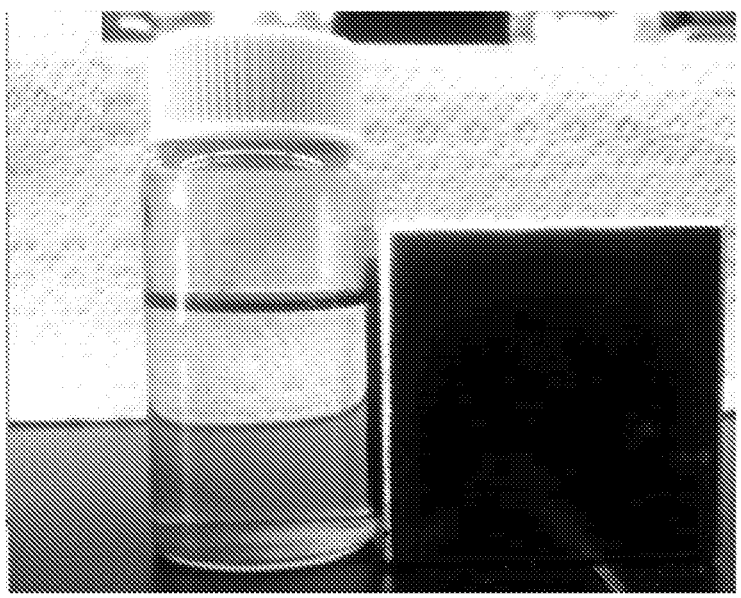

As shown in FIGS. 8A and 8B, photographs of the iron nanoparticle sample showed that the obtained product is black (FIG. 8A), which indicates the generation of pure iron nanoparticles, rather than oxidized $Fe_2O_3$ nanoparticles which are known to be red. The iron nanoparticles exhibited very strong magnetic properties; they responded to a magnet quickly and moved to the side wall of vials within 1-2 seconds (FIG. 8B).

Example 4

Coating the Iron Nanoparticles with Oxides

Figure 9:
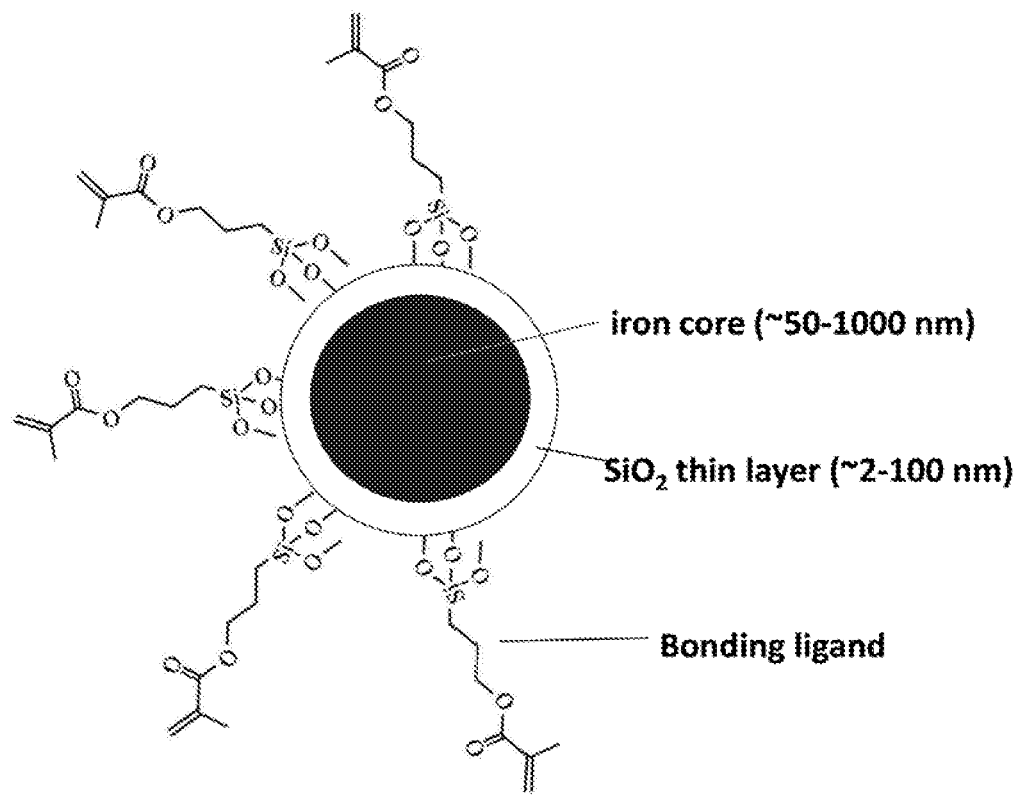
FIG. 9 depicts a schematic illustration of a representative iron nanoparticle coated with silica and bonding ligands.
Figure 10A:
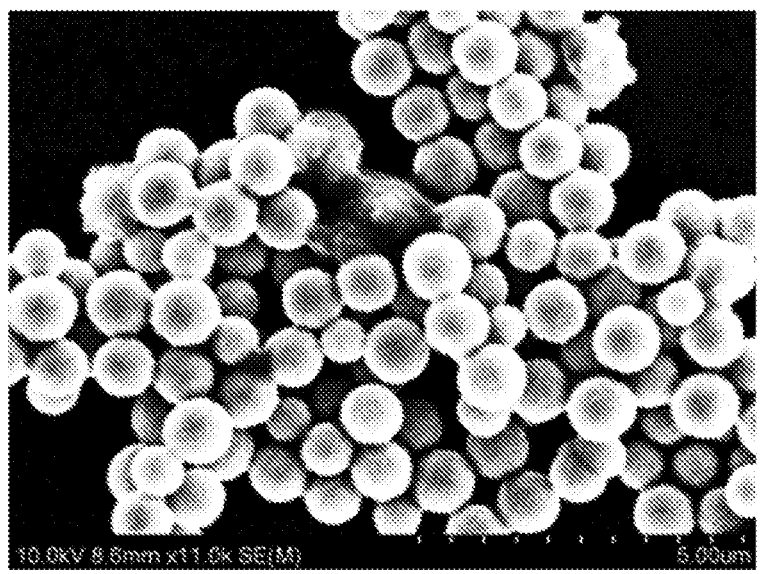
FIGS. 10A-10B are SEM images of iron nanoparticles before (FIG. 10A) and after (FIG. 10B) coating with a silica shell.
Figure 10B:
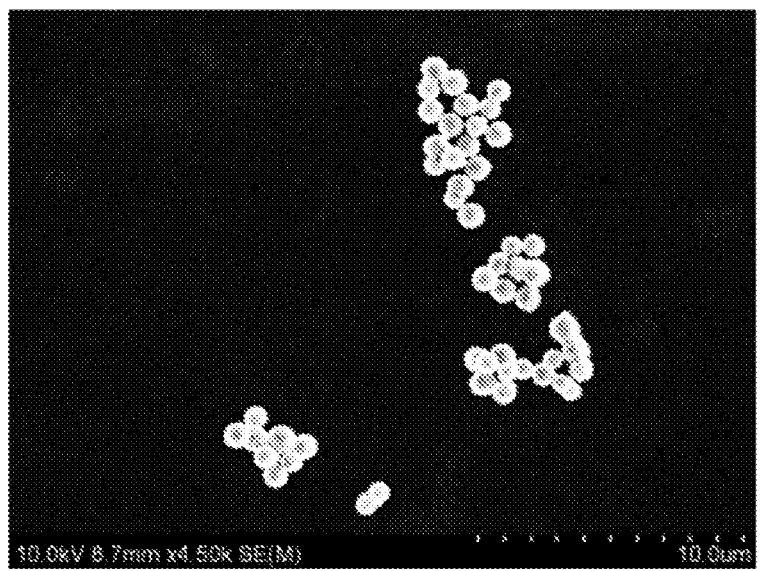
Figure 12:
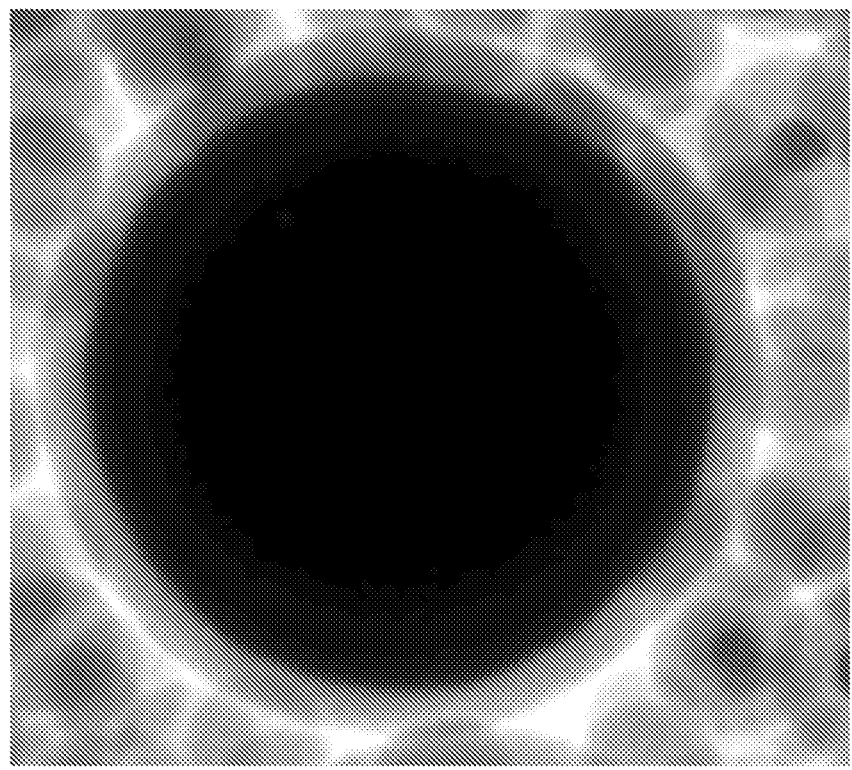
FIG. 12 is a TEM image of an iron nanoparticle coated with a thin layer of silica shell before removing silica nanoparticles (by-product) by magnetic separation.

The surface of iron nanoparticles can be readily coated with oxides of different compositions. Typical oxides that can be coated include $SiO_2$, $ZrO_2$, $TiO_2$, CuO, $Ag_2O$, etc. Provided here is an example of coating with silica oxide. As-prepared iron nanoparticles (55 mg) were dispersed in 80 mL ethanol. 20.0 mL of deionized water and 1.0 mL of ammonium hydroxide solution were added into the dispersion of iron nanoparticles, followed by sonication for 20 minutes. Under vigorous mechanical stirring (560 rpm), a 0.1 mL of TEOS (tetraethyl orthosilicate) was added into the solution at one time. After stirring for 30 minutes, another 0.3 mL of TEOS was added into the reaction. The reaction proceeded at room temperature for 12 hours under continuous mechanical stirring. The silica-coated iron nanoparticles were collected by using a magnet bar and washed with ethanol and water each for 3 times. The thickness of silica layer can be controlled by varying the amount of TEOS added into the reaction. FIG. 9 shows a schematic illustration of a representative iron nanoparticle coated with silica and bonding ligands. FIGS. 10A and 10B show SEM images of iron nanoparticles before and after the coating with silica shell. FIGS. 11A-11F shows a series of representative SEM images of iron nanoparticles with a size of about 300 nm after being coated with a thin layer of silica. The coating of silica on iron nanoparticles is further confirmed by TEM imaging of an iron nanoparticle (FIG. 12).

Example 5

Surface Functionalization of Iron Nanoparticles with Different Organic Ligands

A broad range of organic ligands can be directly functionalized on the surface of iron nanoparticles or through an intermediate layer of oxides. As an example, after coating the iron nanoparticles with silica shell, acrylate functional groups can be introduced onto the surface of nanoparticles through silane chemistry as follows. The Si-coated iron nanoparticles were first dispersed in 50 ml ethanol. Subsequently, a 80 mg of KH570 (3-mercaptopropyl trimethoxysilane) was added into the solution. The solution was sonicated for about 15 minutes. Under vigorous mechanical stirring (560 rpm), the reaction proceeded at room temperature for 48 hours (covered with Alumina foil). The products were collected with a magnet bar and washed with ethanol and water each for 3 times. The acrylate-functionalized magnetic nanoparticles were dispersed in ethanol for further use.

Figure 13:
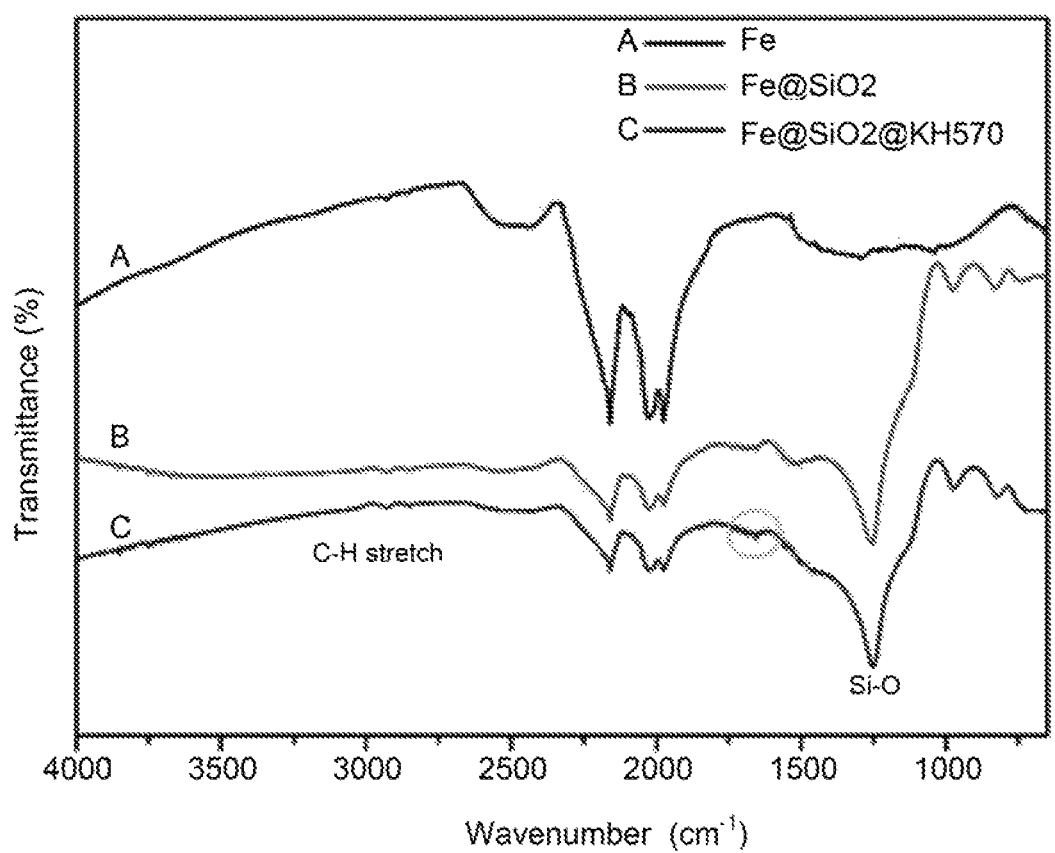
FIG. 13 is a line graph showing the transmittance (%) versus wavenumber ($cm^{-1}$) of the Fourier transform infrared spectroscopy (FT-IR) spectra of iron nanoparticles coated with a thin layer of silica and surface-functionalized with functional groups of polymerizable acrylates: (A) Fe; (B) Fe core with $SiO_2$ shell nanoparticles; (C) Fe core with $SiO_2$ shell nanoparticles functionalized with acrylate group (3-mercaptopropyl trimethoxysilane (KH570, 95%)) on the surface.

The presence of silica and KH570 on the surface of iron nanoparticles was characterized by FT-IR measurement. As shown in FIG. 13, Fe core with $SiO_2$ shell nanoparticles nanoparticles exhibit a clear peak of Si—O—Si (1100 $cm^{-1}$). The same peak also appears in the same nanoparticles surface-grafted with KH570 molecules. This is confirmed by a C—H Stretch peak located at about 2950-2850 ($cm^{-1}$) and a C=O peak located at 1712-2850 ($cm^{-1}$).

Example 6

Continuous Synthesis of Iron Nanoparticles in Flow Reactors

Figure 14:
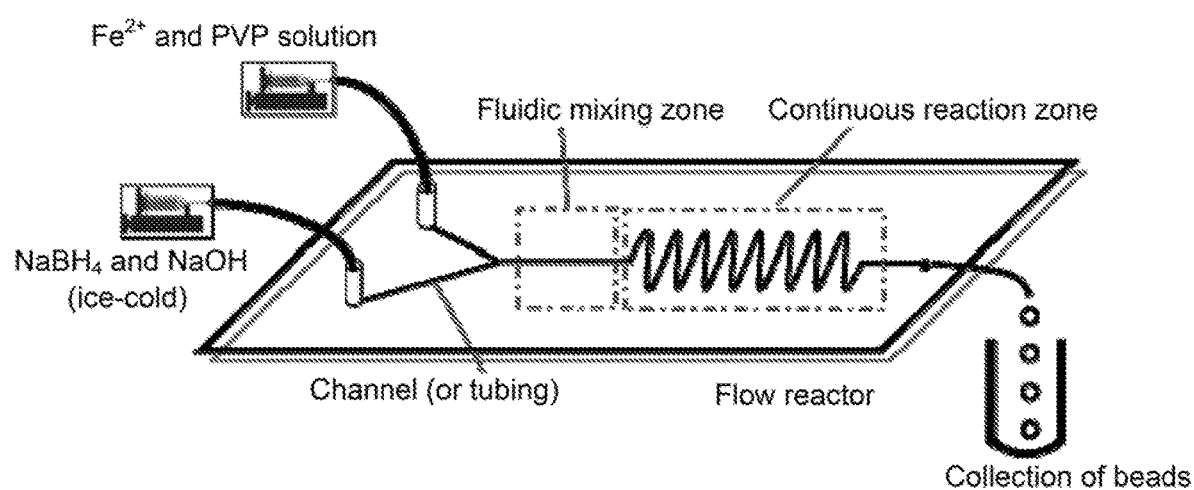
FIG. 14 is a scheme for a continuous synthesis process of iron nanoparticles in a flow tubing reactor.
Figure 15:
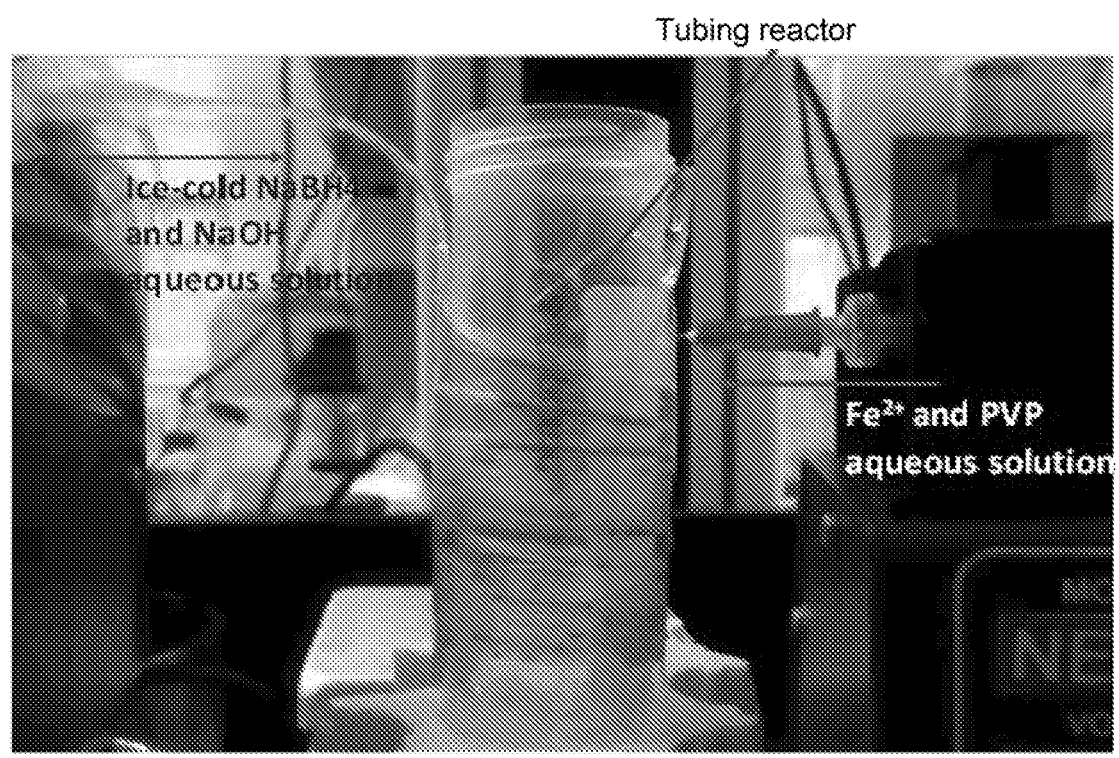
FIG. 15 is a photograph of simple setup for the continuous synthesis process of iron nanoparticles in a flow tubing reactor.

A continuous synthetic approach for the production of iron nanoparticles using flow reactors was developed and is described here. The reactors can be fabricated in plastic chips or constructed from tubings. FIG. 14 shows a schematic illustration of the setup for continuous synthesis. Two solutions (one solution containing $Fe^{2+}$ and PVP and another solution containing NaBH4 and NaOH) were introduced into a tubing using syringe pumps or a pressurized tank. The two solutions were quickly mixed in the mixing zone of the reactor and the reaction proceeded to produce iron nanoparticles in the reaction zone. The dispersion of nanoparticles was collected at the end of the tubing. The size of the iron nanoparticles was controlled by varying the flow rates of the two solutions and the concentration of each of the reactants. A simplified setup of the reactor is shown in FIG. 15. A tubing was used as the reactor and reactants were introduced into the tubing and quickly react to produce iron nanoparticles while flowing downstream. By using this approach, we have produced iron nanoparticles with controllable diameter and narrow size distribution.

Example 7

Development of Magnetic Iron Nanoparticle-Based Dental Adhesive Resins

A novel adhesive resin doped with iron nanoparticles (FIGS. 16A and 16B) was developed. The adhesive doped with iron nanoparticles can be actively steered, using magnetic forces, to enhance infiltration of adhesive resin into dentin. To assess the effect of nanoparticle incorporation on kinetic properties of the adhesive, near infrared spectroscopy (NIR) was used to test the degree of conversion (DC) and polymerization shrinkage stress of the adhesive resin. Several formulations with various nanoparticle sizes and concentration were prepared and tested.

Figure 17A:
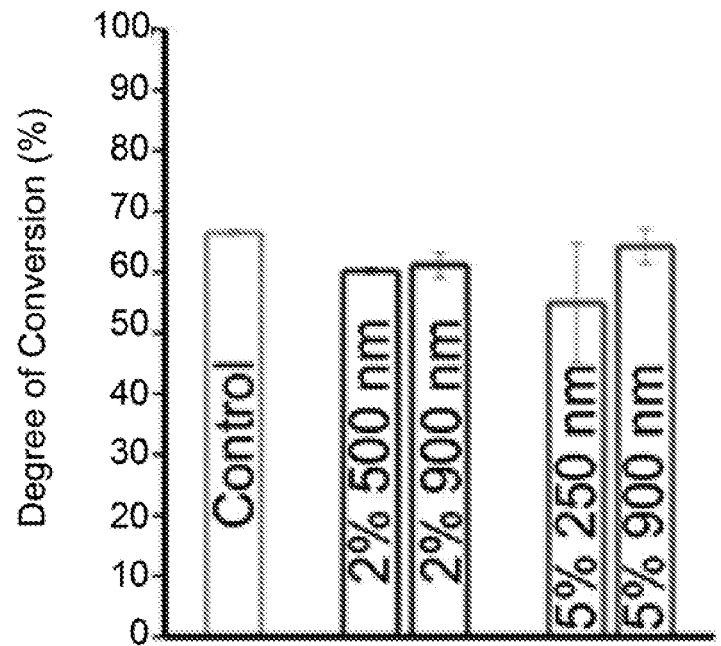
FIG. 17A is a bar graph showing Degree of Conversion of iron nanoparticle-doped adhesive resins with different nanoparticle sizes and concentrations compared to the control (adhesives with no nanoparticles).
Figure 17B:
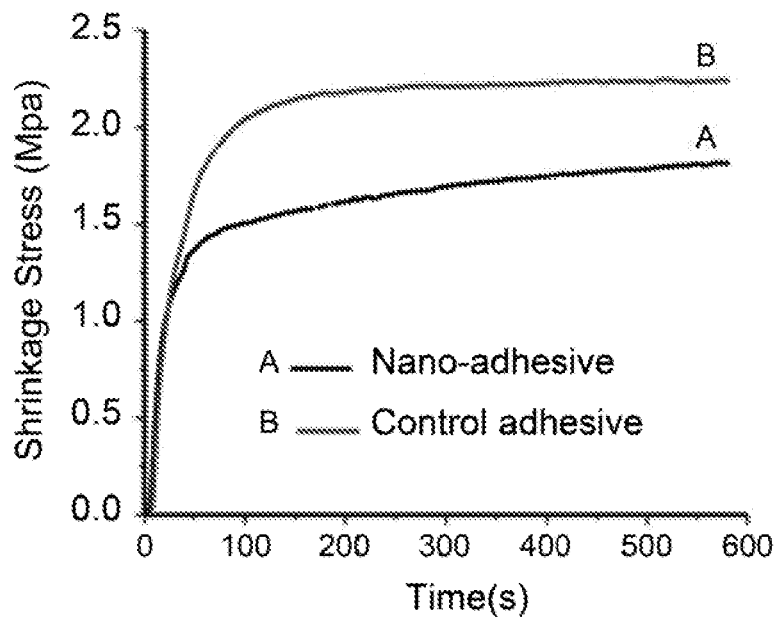
FIG. 17B is a line graph showing the Shrinkage Stress (MPa) versus Time (s) of iron nanoparticle-doped adhesive resins (adhesive with 5 wt % of 900 nm nanoparticle) compared to the control (adhesives with no nanoparticles).

As shown in FIGS. 17A and 17B, the DC was influenced by the nanoparticle size and concentration, but in general, the DC values were comparable to those described for commercial adhesives. For example, the DC for the 900 nm nanoparticle-doped adhesive (5 wt %.) appeared to be comparable to that of the control adhesive without nanoparticles. However, the same nanoparticle-doped adhesive (900 nm, 5 wt %) was associated with smaller polymerization shrinkage stress than the control (FIG. 17B).

Figure 18A:
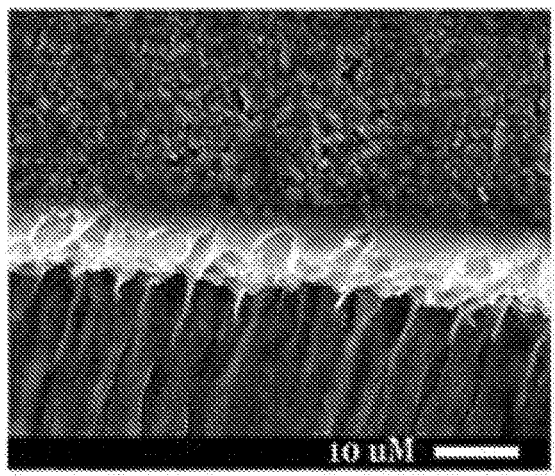
FIGS. 18A-18D are SEM images of representative examples from teeth restored using control adhesive (FIG. 18A), iron nanoparticle-doped adhesive resin with no magnetic pull (FIG. 18B), iron nanoparticle-doped adhesive resin with a 60 second magnetic pull (FIG. 18C), and an enlarged image of FIG. 18C highlighting the horizontal cross-linking (white arrows) (FIG. 18D). Density of resin tags formed by the iron nanoparticle-doped adhesive resin suggested superior infiltration (FIG. 18D).
Figure 18B:
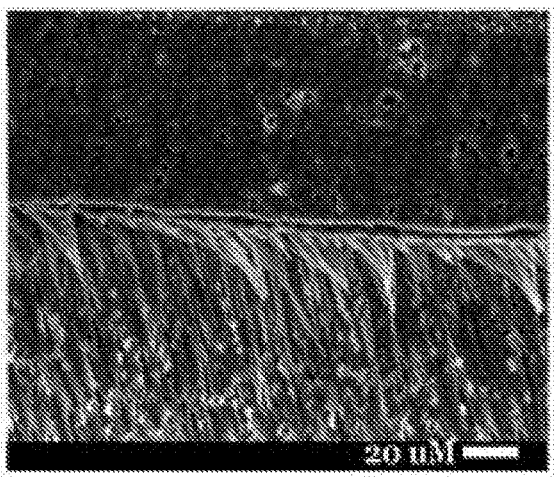
Figure 18C:
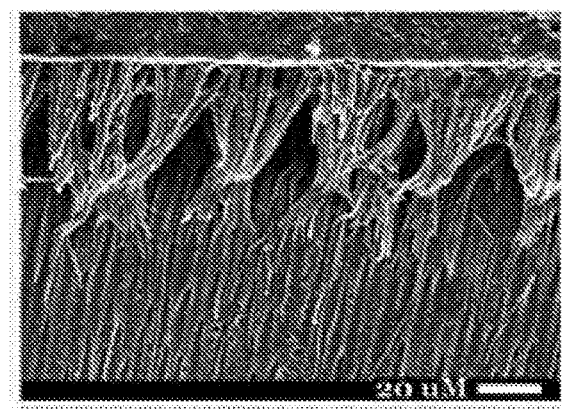
Figure 18D:
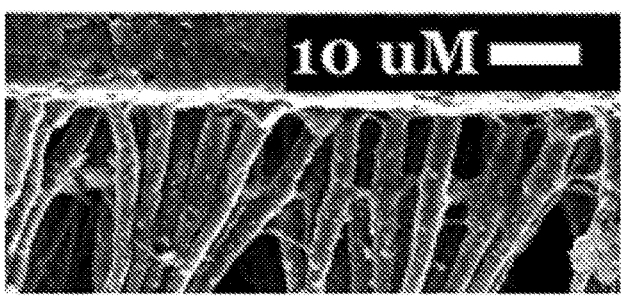

Preliminary experiments were performed to test if the use of short magnetic force improves the penetration of the adhesive into dentin and dentinal tubules. Recently extracted human third molar teeth were obtained and the occlusal third of the crown was removed to expose dentin. The exposed dentin was polished and etched. The prepared teeth were divided randomly into three groups (n=5/group): (1) teeth restored using control adhesive (no nanoparticles and no magnetic pull applied); (2) teeth restored using our nanoparticle-doped adhesive (900 nm) and no magnetic pull; and (3) teeth restored using the nanoparticle-doped adhesive resin and 60 second magnetic pull. To apply magnetic pull, an off-the-shelf magnet (1.2 T) was placed directly under the teeth, 25 mm from the occlusal surface of the dentin, for 60 seconds while the adhesive was being applied. The adhesive was then cured for 10 seconds and composite resin applied and cured. The teeth were then sectioned to examine the resin/dentin interface using a scanning electron microscope (SEM). Representative examples are shown in FIGS. 18A-FIG. 18D. Visual inspection of these images revealed that the teeth treated with the magnetic iron nanoparticle-doped adhesive system demonstrated better penetration of adhesive resin as evidenced by the denser and longer resin tags. The images also showed evidence of cross-linking between resin tags when the novel iron nanoparticle-doped adhesive was used (FIG. 18D). The average depth and the total number of resin tags per field of view ("density" of resin tags) were quantified in these teeth. It was found that average length and density of resin tags were greater when magnetic pull was applied (FIG. 19A and FIG. 19B). These findings suggest that the iron nanoparticle-doped adhesive system not only increases the penetration of the adhesive into dentinal tubules, but it also increases the probability that a resin tag forms.

The effect of magnetic nanoparticle-adhesive system on the shear bond strength of composite resin to dentin was also tested. The teeth were prepared as described above for SEM examination with one modification: a metal ring was used to control and standardize the area restored with the composite. The shear bond strength of composite to dentin, using the novel magnetic nanoparticle adhesive (900 nm), was double that of the controls (FIG. 19C). In conclusion, these findings suggest that the incorporation of iron nanoparticles into dental adhesive results in superior bond strength. The microtensile bond strength, flexural strength, and both fatigue strength and fatigue crack growth resistance of the interface were also tested.

In related studies investigating the biocompatibility of nanoparticles in dental applications, in vivo experiments were performed to evaluate the effect of nanoparticles on pro-inflammatory cytokine production in rat teeth.

Figure 20A:
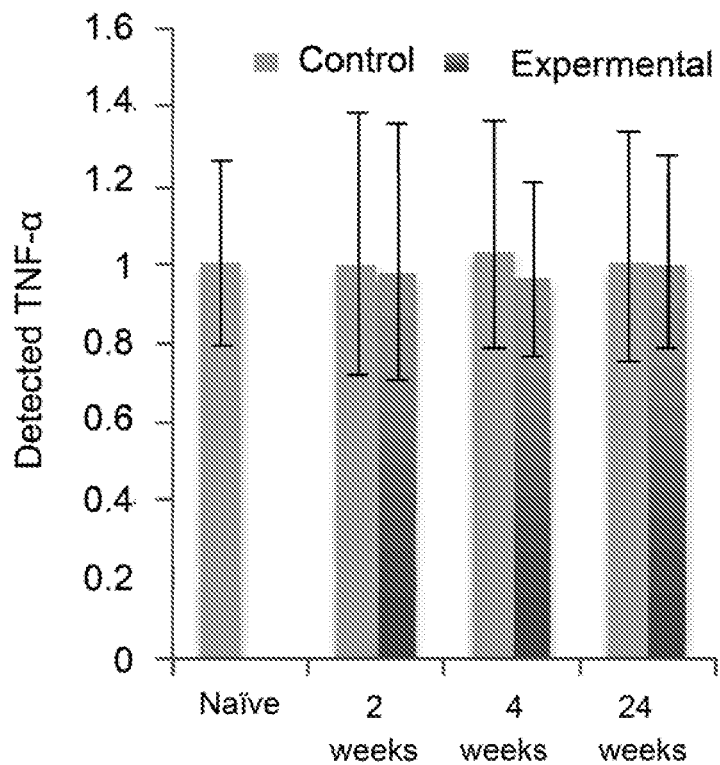
FIG. 20A is a bar graph showing detected tumor necrosis factor alpha (TNF-α) at various time points after pull of nanoparticles into pulp.
Figure 20B:
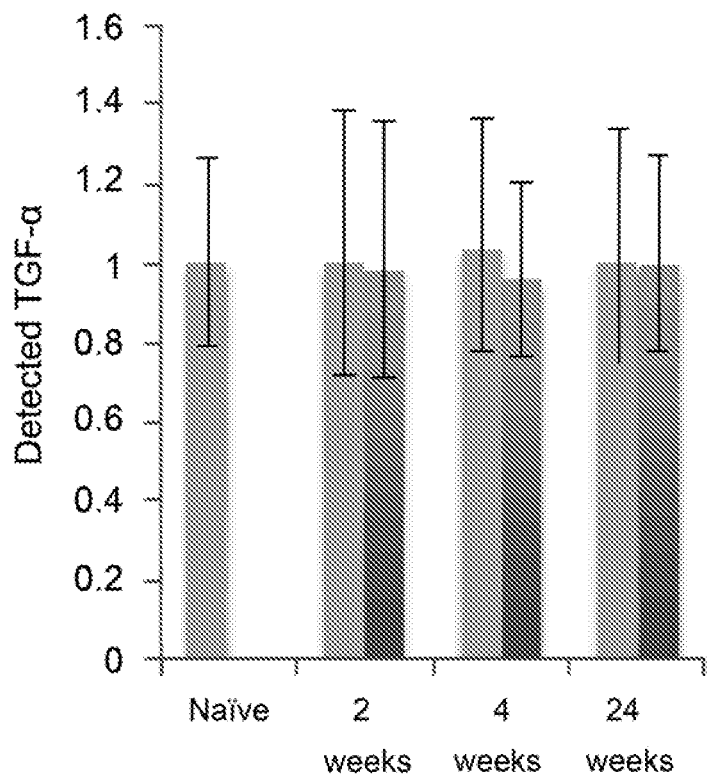
FIG. 20B is a bar graph showing detected transforming growth factor alpha (TGF-α) at various time points after pull of nanoparticles into pulp. No significant differences were detected in TNF-α (FIG. 20A, p=0.65) and TGF-α (FIG. 20B, p=0.78) in rat molar pulp tissue at various time points after pull of nanoparticles into pulp. Control: nanoparticles without magnetic pull, Experimental: nanoparticles with magnetic pull.

Experimental cavities in rat mandibular molars were prepared and a sterile saline solution was applied containing iron nanoparticles coated with polysaccharides (no adhesive was tested). A magnet was used to pull the iron nanoparticles into the pulp through dentinal tubules. Magnetic forces for extended periods (30 min.) were used to test the ability to deliver a large amount of nanoparticles to the pulp. After the delivery of nanoparticles, the teeth were restored with composite resin and the animals were allowed to survive for 2, 4 or 24 weeks. Pulpal tissues were extracted from the teeth after these time points and qRT-PCR was used to assess the expression of pro-inflammatory cytokines as indicators of pulpal inflammation. Cytokines involved in both the acute and chronic phases of the immune response including tumor necrosis factor alpha (TNF-α) and transforming growth factor alpha (TGF-α) were studied. No significant differences in cytokines were detected in the pulp of teeth treated with these nanoparticles compared to controls (nanoparticles but no pull), and compared to untreated teeth (n=8 animals/group, FIG. 20A, p=0.65 and FIG. 20B, p=0.78). These findings suggest that iron nanoparticles are not detrimental to the pulp. The effect of the iron nanoparticle-doped adhesive system on the production of several pulpal cytokines was tested over a longer follow-up period. The longevity of composite restorations in rat teeth was assessed and histological examination of pulpal tissues adjacent to composite restoration were performed.

REFERENCES

1. Hikaru Aoshima, Hironobu Suzuki, Hiroshi Sakuma, and Kiyoshi Ishii, Fabrication of Fe nanoparticles with sizes ranging from 30 to 170 nm by gas flow sputtering. Journal of Applied Physics, 2009. 105(7):07B519.
2. Dale L Huber, Synthesis, Properties, and Applications of Iron Nanoparticles. Small, 2005. 1(5):482-501.
3. Sheng Peng, Chao Wang, Jin Xie, and Shouheng Sun, Synthesis and Stabilization of Monodisperse Fe Nanoparticles. Journal of the American Chemical Society, 2006. 128(33):10676-10677.
4. Genban Sun, Bingxiang Dong, Minhua Cao, Bingqing Wei, and Changwen Hu, Hierarchical Dendrite-Like Magnetic Materials of $Fe_3O_4$, γ-$Fe_2O_3$, and Fe with High Performance of Microwave Absorption. Chemistry of Materials, 2011. 23(6):1587-1593.
5. Li-Shun Fu, Jian-Tang Jiang, Cheng-Yan Xu, and Liang Zhen, Synthesis of hexagonal Fe microflakes with excellent microwave absorption performance. CrystEngComm, 2012. 14(20):6827-6832.
6. Liqun Wang, Xuegang Lu, Chang Han, Ruie Lu, Sen Yang, and Xiaoping Song, Electrospun hollow cage-like [small alpha]-$Fe_2O_3$ microspheres: synthesis, formation mechanism, and morphology-preserved conversion to Fe nanostructures. CrystEngComm, 2014. 16(46):10618-10623.
7. Liqun Wang, Xuegang Lu, Jieqiong Wang, Sen Yang, and Xiaoping Song, Facile synthesis of Fe@$Fe_2O_3$ nanochains exhibiting high heating efficiency in magnetic hyperthermia. Journal of Alloys and Compounds.
8. Xiaotong Zhan, Hongzhe Tang, Yu Du, Adbrimkrim Talbi, Jinlong Zha, and Junhui He, Facile preparation of Fe nanochains and their electromagnetic properties. RSC Advances, 2013. 3(36):15966-15970.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications, and publications cited herein are fully incorporated by reference herein in their entirety.

What is claimed is:

1. A process for the preparation of iron nanoparticles, comprising reacting a $Fe^{2+}$ salt with a reducing agent in the presence of a polymer surfactant and a base, wherein the iron nanoparticles have a diameter of between about 200 nm and about 1000 nm, and wherein the reacting is carried out in aqueous solution.

2. The process of claim 1, wherein the $Fe^{2+}$ salt is selected from the group consisting of $FeCl_2$, $FeBr_2$, $FeI_2$, and $Fe(SO_4)_2$.

3. The process of claim 1, wherein the reducing agent is selected from the group consisting of $NaBH_4$, $LiBH_4$, $N_2H_4$, $NaH_2PO$, $NaBH_3CN$, $NaBH(OAc)_3$, a sulfite, and an amino acid.

4. The process of claim 1, wherein the polymer surfactant is selected from the group consisting of polyvinylpyrrolidone (PVP), polyacrylic acid, polystyrene sulfonate, poly (allylamine hydrochloride), polyvinyl alcohol, poly(methacrylic acid), polyaspartic acid, poly(2-acrylamido-2-methyl-1-propanesulfonic acid), polyacrylamide, polypeptides, glycosaminoglycans, Triton X-100, polyethylene glycol nonyl phenyl ether, and a deoxyribonucleic acid.

5. The process of claim 4, wherein the polymer surfactant is a PVP having a number average molecular weight of 1 to 80 kilodaltons.

6. The process of claim 1, wherein the base is aqueous NaOH or KOH.

7. The process of claim 1, wherein the concentration of polymer surfactant in water is 0.001 to 0.100 g/mL, the concentration of reducing agent is 0.01 to 1.0 M, and the concentration of base is 0.0001 to 1.0 M.

8. The process of claim 7, wherein the polymer surfactant is PVP of 40 kilodaltons having a concentration of about 0.03 g/mL, the reducing agent is $NaBH_4$ having a concentration of about 0.1 M, and the base is NaOH having a concentration of about 0.6 mM to about 1.3 mM.

* * * * *